US008309748B2

(12) United States Patent
Ding et al.

(10) Patent No.: US 8,309,748 B2
(45) Date of Patent: Nov. 13, 2012

(54) HALF-METALLOCENE COMPOUNDS AND CATALYST COMPOSITIONS

(75) Inventors: Errun Ding, Bartlesville, OK (US); Joel L. Martin, Bartlesville, OK (US); Albert P. Masino, Tulsa, OK (US); Qing Yang, Bartlesville, OK (US); Youlu Yu, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 65 days.

(21) Appl. No.: 13/013,106

(22) Filed: Jan. 25, 2011

(65) Prior Publication Data

US 2012/0190803 A1 Jul. 26, 2012

(51) Int. Cl.
*C07F 17/00* (2006.01)
*C08F 4/6592* (2006.01)
(52) U.S. Cl. ............ 556/53; 526/160; 526/165; 526/943
(58) Field of Classification Search .................... 556/53; 526/160, 165, 943
See application file for complete search history.

(56) References Cited

U.S. PATENT DOCUMENTS

| | | | |
|---|---|---|---|
| 3,242,099 A | 3/1966 | Manyik | |
| 3,248,179 A | 4/1966 | Norwood | |
| 4,060,480 A | 11/1977 | Reed | |
| 4,452,910 A | 6/1984 | Hopkins | |
| 4,501,885 A | 2/1985 | Sherk | |
| 4,588,790 A | 5/1986 | Jenkins | |
| 4,794,096 A | 12/1988 | Ewen | |
| 4,808,561 A | 2/1989 | Welborn | |
| 4,871,705 A | 10/1989 | Hoel | |
| 4,939,217 A | 7/1990 | Stricklen | |
| 5,332,706 A | 7/1994 | Nowlin et al. | |
| 5,352,749 A | 10/1994 | DeChellis | |
| 5,376,611 A | 12/1994 | Shveima | |
| 5,436,304 A | 7/1995 | Griffin | |
| 5,455,314 A | 10/1995 | Burns | |
| 5,539,076 A | 7/1996 | Nowlin et al. | |
| 5,556,821 A | 9/1996 | Aida et al. | |
| 5,565,175 A | 10/1996 | Hottovy | |
| 5,575,979 A | 11/1996 | Hanson | |
| 5,576,259 A | 11/1996 | Hasegawa | |
| 5,635,573 A | 6/1997 | Harrington et al. | |
| 5,698,651 A | 12/1997 | Kawasaki et al. | |
| 5,739,220 A | 4/1998 | Shamshoum et al. | |
| 5,747,405 A | 5/1998 | Little et al. | |
| 5,807,938 A | 9/1998 | Kaneko | |
| 5,861,352 A | 1/1999 | Gila et al. | |
| 5,906,955 A | 5/1999 | Hamura et al. | |
| 5,919,983 A | 7/1999 | Rosen | |
| 5,942,459 A | 8/1999 | Sugano et al. | |
| 5,962,362 A | 10/1999 | Wasserman et al. | |
| 6,107,230 A | 8/2000 | McDaniel et al. | |
| 6,127,302 A | 10/2000 | Wasserman | |
| 6,159,889 A | 12/2000 | Wasserman | |
| 6,165,929 A | 12/2000 | McDaniel | |
| 6,239,235 B1 | 5/2001 | Hottovy | |
| 6,242,622 B1 | 6/2001 | Oda et al. | |
| 6,262,191 B1 | 7/2001 | Hottovy | |
| 6,294,494 B1 | 9/2001 | McDaniel | |
| 6,300,271 B1 | 10/2001 | McDaniel | |
| 6,316,553 B1 | 11/2001 | McDaniel | |
| 6,340,652 B1 | 1/2002 | Sugano et al. | |
| 6,355,594 B1 | 3/2002 | McDaniel | |
| 6,376,415 B1 | 4/2002 | McDaniel | |
| 6,388,017 B1 | 5/2002 | McDaniel | |
| 6,391,816 B1 | 5/2002 | McDaniel | |
| 6,395,666 B1 | 5/2002 | McDaniel | |
| 6,410,657 B1 | 6/2002 | Ko et al. | |
| 6,469,117 B1 | 10/2002 | Kuang et al. | |
| 6,524,987 B1 | 2/2003 | Collins | |
| 6,528,448 B1 | 3/2003 | Jensen et al. | |
| 6,531,550 B1 | 3/2003 | McDaniel et al. | |
| 6,548,441 B1 | 4/2003 | McDaniel | |
| 6,548,442 B1 | 4/2003 | McDaniel et al. | |
| 6,576,583 B1 | 6/2003 | McDaniel | |
| 6,613,712 B1 | 9/2003 | McDaniel | |
| 6,632,894 B1 | 10/2003 | McDaniel | |
| 6,667,274 B1 | 12/2003 | Hawley | |
| 6,750,302 B1 | 6/2004 | McDaniel | |
| 6,825,369 B1 | 11/2004 | Stevens et al. | |
| 6,831,141 B2 | 12/2004 | McDaniel et al. | |
| 6,833,415 B2 | 12/2004 | Kendrick | |
| 6,982,306 B2 | 1/2006 | Martin et al. | |
| 7,226,886 B2 | 6/2007 | Jayaratne et al. | |
| 7,294,599 B2 | 11/2007 | Jensen et al. | |

(Continued)

FOREIGN PATENT DOCUMENTS

EP 0 989 139 A1 3/2000

(Continued)

OTHER PUBLICATIONS

Kotohiro Nomura, et al., Article entitled Syndiospecific Styrene Polymerization and Efficient Ethylene/Styrene Copolymerization Catalyzed by (Cyclopentadienyl)(aryloxy)titanium(IV) Complexes—MAO System, published in *Macromolecules* 2000, 33, pp. 8122-8124.

Kotohiro Nomura, et al., Article entitled "Ethylene/α-olefin copolymerization by various nonbridged (cyclopentadienyl)(aryloxy)titanium(IV) complexes—MAO catalyst system," published in *Journal of Molecular Catalysis A: Chemical 174* (2001), pp. 127-140.

Andrew E. Fenwick, et al., Article entitled "Formation of Neutral and Cationic Methyl Derivatives of Titanium Containing Cyclopentadienyl and Aryolxide Ancillary Ligation," published in *Organomettalics* 2004, 23, pp. 2146-2156.

Doo Jin Byun, et al., Article entitled "Effect of Cyclopentadienyl and Anionic Ancillary Ligand in Syndiospecific Styrene Polymerization Catalyzed by Nonbridged Half-Titanocenes Containing Aryloxo, Amide, and Anilide Ligands: Cocatalyst Systems," published in *Macromolecules* 2004, 37, pp. 5520-5530.

(Continued)

*Primary Examiner* — Caixia Lu

(74) *Attorney, Agent, or Firm* — Merchant & Gould P.C.

(57) ABSTRACT

The present invention provides polymerization catalyst compositions employing half-metallocene compounds with a heteroatom-containing ligand bound to the transition metal. Methods for making these hybrid metallocene compounds and for using such compounds in catalyst compositions for the polymerization of olefins also are provided.

22 Claims, 8 Drawing Sheets

U.S. PATENT DOCUMENTS

| | | | |
|---|---|---|---|
| 7,390,764 | B2 | 6/2008 | McDaniel et al. |
| 7,417,097 | B2 | 8/2008 | Yu et al. |
| 7,601,665 | B2 | 10/2009 | McDaniel et al. |
| 7,763,561 | B2 | 7/2010 | McDaniel et al. |
| 7,884,165 | B2 | 2/2011 | McDaniel et al. |
| 2004/0059070 | A1 | 3/2004 | Whitte et al. |
| 2005/0113243 | A1 | 5/2005 | Thorn et al. |
| 2010/0010174 | A1 | 1/2010 | McDaniel et al. |
| 2010/0076167 | A1 | 3/2010 | McDaniel et al. |
| 2010/0317904 | A1 | 12/2010 | Small |
| 2011/0082323 | A1 | 4/2011 | Small et al. |

FOREIGN PATENT DOCUMENTS

| | | |
|---|---|---|
| EP | 1 102 795 A1 | 5/2001 |
| JP | 11 166010 A | 6/1999 |
| WO | WO 2004/018489 A1 | 3/2004 |
| WO | WO2005/075526 | 8/2005 |
| WO | WO2006/012321 | 2/2006 |
| WO | WO2010/008515 | 1/2010 |

OTHER PUBLICATIONS

Kotohiro Nomura, et al., Article entitled "Effect of aryloxide ligand in 1-hexene, styrene polymerization catalyzed by nonbridged half-titanocenes of the type, Cp'TiCl$_2$(OAr) (Cp'=C$_5$Me$_5$, $^t$BuC$_5$H$_4$) Structural analyses for Cp*TiCl$_2$(O-2,6-$^t$Bu$_2$C$_6$H$_3$) and Cp*TiCl$_2$(O-2,6-$^i$Pr$_2$-4-$^t$BuC$_6$H$_2$)," published in *Journal of Molecular Catalysis A: Chemical 254* (2006), pp. 197-205.

Khamphee Phomphrai, et al., Article entitled "Diverse Pathways of Activation and Deactivation of Half-Sandwich Aryloxide Titanium Polymerization Catalysts," published in *Organometallics* 2006, 25, pp. 214-220.

Thomas A. Manz, et al., Article entitled "Structure-Activity Correlation in Titanium Single-Site Olefin Polymerization Catalysts Containing Mixed Cyclopentadienyl/Aryloxide Ligation," published in *J. Am. Chem. Soc.*, 2007, pp. S1-1 through S1-30.

Koji Itagaki, et al., Article entitled "Ethylene polymerization and ethylene/1-octene copolymerization using group 4 half-metallocenes containing aryloxo ligands, Cp*MCl$_2$(OAr) [M=Ti, Zr, Hf; Ar=O-2,6-R$_2$C$_6$H$_3$, R=$^t$Bu, Ph]—MAO catalyst systems," published in *Journal of Molecular Catalysis A: Chemical 303* (2009); pp. 102-109.

Christopher P. Nicholas, et al., Article entitled "Synthesis, Spectroscopy, and Catalytic Properties of Cationic Organozirconium Adsorbates on "Super Acidic" Sulfated Alumina. "Single-Site" Heterogeneous Catalysts with Virtually 100% Active Sites," published in *J. Am. Chem. Soc.* 2003, 125, pp. 4325-4331.

Christopher P. Nicholas, et al., Article entitled "Zirconium Hydrocarbyl Chemisorpotion on Sulfated Metal Oxides: New Supports, Chemisorption Pathways, and Implications for Catalysis," published in *Langmuir* 2004, 20, pp. 9456-9462.

*Modern Plastics Encyclopedia '96*, Mid-Nov. 1995 Issue, vol. 72, No. 12; 3 pages.

*Film Extrusion Manual—Process, Materials, Properties*, TAPPI Press, 1992; pp. ix-xxiiii; 16 pages.

Wyatt, P.J., *Anal. Chim. Acta*, 272, 1 (1993), 40 pages.

Manz et al., "Supporting Information Part 1: Experimental Details, Kinetic Analysis, and Model Optimization," J. Am. Chem. Soc. 2007, vol. 129, pp. 3776-3777.

Arevalo et al., "Ethylene polymerization behavior of monometallic complexes and metallodendrimers based on cyclopentadienyl-aryloxy titanium units," Journal of Organometallic Chemistry, 2005, 690, pp. 4620-4627.

Antinolo et al., "Synthesis of Zirconium (IV) Monocyclopentadienyl-Aryloxy Complexes and Their Use in Catalytic Ethylene Polymerization. X-ray Structure of ($\eta^5$-C$_5$Me$_5$)Zr{2,6-OC$_6$H$_3$(CH$_3$)$_2$}$_3$," Organometallics, 2000, 19, pp. 2837-2843.

Arevalo et al., "Synthesis of Aryloxo Cyclopentadienyl Group 4 Metal-Containing Dendrimers, Organometallics," 2003, 22, pp. 5109-5113.

Hieber et al., "Some correlations involving the shear viscosity of polystyrene melts," Rheologica Acta 28 (1989), pp. 321-332.

Hieber et al., "Shear-Rate-Dependence Modeling of Polymer Melt Viscosity," Polymer Engineering and Science 1992, vol. 32, No. 14, pp. 931-938.

Bird et al., "Dynamics of Polymeric Liquids," vol. 1, Fluid Mechanics, 2nd Edition, John Wiley & Sons (1987), 3 pages.

Thorn, Matthew G., Synthesis, Characterization, and One-Electron Reduction of Mixed-Cyclopentadienyl/Aryloxide Titanium Dichlorides, Orgonometallics 2000, vol. 19, No. 26, 5636-5642.

International Search Report for Application No. PCT/US2009/004047, mailed Dec. 10, 2009, 4 pages.

Cotton et al., Advanced Inorganic Chemistry, 6th Ed., Wiley-Interscience, 1999, 4 pages.

Hawley's Condensed Chemical Dictionary, 11th Ed., John Wiley & Sons, 1995, 3 pages.

Li, et al., Coordination Copolymerization of Severely Encumbered Isoalkenes with Ethylene: Enhanced Enchainment Mediated by Binuclear Catalysts and Cocatalysts, JACS Articles, 2005, 127, 14756-14768.

Pinnavaia, "Intercalated Clay Catalysts," Science, 1983, 220(4595), pp. 365-371.

Scholz et al., "Benzylverbindungen elektronenarmer Übergangsmetalle . . .," Journal of Organometallic Chemistry 1993, vol. 443, pp. 93-99.

Thomas, "Sheet Silicate Intercalates: New Agents for Unusual Chemical Conversions," Intercalation Chemistry (S. Whittington and A. Jacobson, eds.), Academic Press, Inc. Ch. 3, 1972, pp. 55-99.

Thorn et al., "Synthesis, structure and molecular dynamics of $\eta^2$—iminoacyl . . . ," Journal of the Chemical Society, Dalton Transactions 2002, vol. 17, pp. 3398-3405.

International Search Report, PCT/US2012/022311, dated Apr. 2, 2012.

Sturla SJ, et al., Monocyclopentadienyltitanium Aryloxide Complexes: Preparation, Characterization, and Application in Cyclization Reactions, *Organometallics*, vol. 21, No. 4, pp. 739-748 (Feb. 18, 2002).

HALF-METALLOCENE COMPOUNDS AND CATALYST COMPOSITIONS

BACKGROUND OF THE INVENTION

The present invention relates generally to the field of olefin polymerization catalysis, catalyst compositions, methods for the polymerization of olefins, and polyolefins. More specifically, this invention relates to half-metallocene compounds with a heteroatom-containing ligand bound to the transition metal, and catalyst compositions employing such hybrid compounds.

Polyolefins such as high density polyethylene (HDPE) homopolymer and linear low density polyethylene (LLDPE) copolymer can be produced using various combinations of catalyst systems and polymerization processes. One method that can be used to produce such polyolefins employs a chromium-based catalyst system. HDPE and LLDPE resins produced using a chromium-based catalyst system generally have a broad molecular weight distribution. For instance, resins having a polydispersity index (PDI, or Mw/Mn) greater than 6 are not unusual. Polyolefin resins produced using a chromium catalyst also can have a low level of long chain branching. This combination of properties is difficult to duplicate with other commercially viable catalyst systems. Metallocene catalysts, for example, generally can produce polyolefins with a much narrower molecular weight distribution and either have too little, or too much, long chain branching. Likewise, Ziegler-type catalyst systems can produce polyolefin resins which are typically much narrower in molecular weight distribution and have substantially no long chain branching. Polyolefin resins produced using a Ballard type catalyst generally can be too high in molecular weight, too broad in molecular weight distribution, and contain too much long chain branching.

It would be beneficial to have a non-chromium catalyst system that could produce an olefin polymer having the desired combination of a relatively broad molecular weight distribution and a relatively low level of long chain branching. Accordingly, it is to this end that the present invention is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention generally relates to new catalyst compositions, methods for preparing catalyst compositions, methods for using the catalyst compositions to polymerize olefins, the polymer resins produced using such catalyst compositions, and articles produced using these polymer resins. In particular, the present invention relates to half-metallocene compounds with a heteroatom-containing ligand bound to the transition metal, and catalyst compositions employing such hybrid metallocene compounds. Catalyst compositions of the present invention which contain these hybrid metallocene compounds can be used to produce, for example, ethylene-based homopolymers and copolymers.

Disclosed and described herein are novel hybrid metallocene compounds having a metallocene moiety and a heteroatom-containing ligand. According to one aspect of the present invention, these unbridged hybrid metallocene compounds can have the formula:

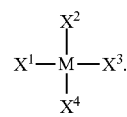

(I)

In formula (I), M can be Zr, Hf, or Ti; $X^1$ and $X^2$ independently can be a halide or a substituted or unsubstituted aliphatic, aromatic, or cyclic group, or a combination thereof; $X^3$ can be a substituted or unsubstituted cyclopentadienyl, indenyl, or fluorenyl group, wherein any substituents on $X^3$ independently are a hydrogen atom or a substituted or unsubstituted aliphatic, aromatic, or cyclic group, or a combination thereof; and $X^4$ can be —O—$R^A$, —NH—$R^A$, —PH—$R^A$, —S—$R^A$, —O—Si—$R^B{}_3$, or —O—C—$R^B{}_3$. $R^A$ can be an aryl group substituted with a first alkoxy group and a second substituent selected from an alkyl, cycloalkyl, or second alkoxy group, wherein any additional substituents on $R^A$ independently are a hydrogen atom or an alkyl, cycloalkyl, or alkoxy group. Each $R^B$ independently can be a hydrogen atom or a substituted or unsubstituted aliphatic, aromatic, or cyclic group, or a combination thereof.

Catalyst compositions containing these unbridged hybrid metallocene compounds are also provided by the present invention. In one aspect, a catalyst composition is disclosed which comprises a hybrid metallocene compound and an activator. This catalyst composition can further comprise an organoaluminum compound. In some aspects, the activator can comprise an activator-support, while in other aspects, the activator can comprise an aluminoxane compound, an organoboron or organoborate compound, an ionizing ionic compound, or combinations thereof.

In accordance with certain aspects of the invention, novel hybrid metallocene compounds and catalyst compositions comprising these hybrid metallocene compounds and an activator are disclosed and described. For instance, these hybrid metallocene compounds can have one of the following formulas:

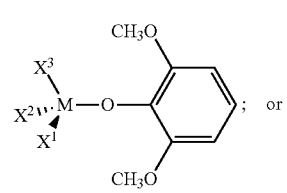

(III)

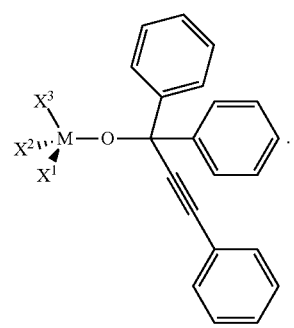

(IV)

In formula (III) and formula (IV), each M independently can be Zr, Hf, or Ti; each $X^1$ and $X^2$ independently can be a halide or a substituted or unsubstituted aliphatic, aromatic, or cyclic group, or a combination thereof; and each $X^3$ independently can be a substituted or unsubstituted cyclopentadienyl, indenyl, or fluorenyl group, wherein any substituents on $X^3$ independently are a hydrogen atom or a substituted or unsubstituted aliphatic, aromatic, or cyclic group, or a combination thereof.

Catalyst compositions containing a hybrid metallocene compound having formula (III) or formula (IV) can further comprise an organoaluminum compound, and the activator can comprise an activator-support, an aluminoxane compound, an organoboron or organoborate compound, an ionizing ionic compound, or combinations thereof.

The present invention also contemplates olefin polymerization processes. Such processes can comprise contacting a catalyst composition with an olefin monomer and optionally an olefin comonomer under polymerization conditions to produce an olefin polymer. Generally, the catalyst composition employed can comprise any of the hybrid metallocene compounds disclosed herein and any of the activators disclosed herein. Further, organoaluminum compounds also can be utilized in the polymerization processes.

Polymers produced from the polymerization of olefins, resulting in homopolymers, copolymers, terpolymers, etc., can be used to produce various articles of manufacture.

DEFINITIONS

Figure 1:
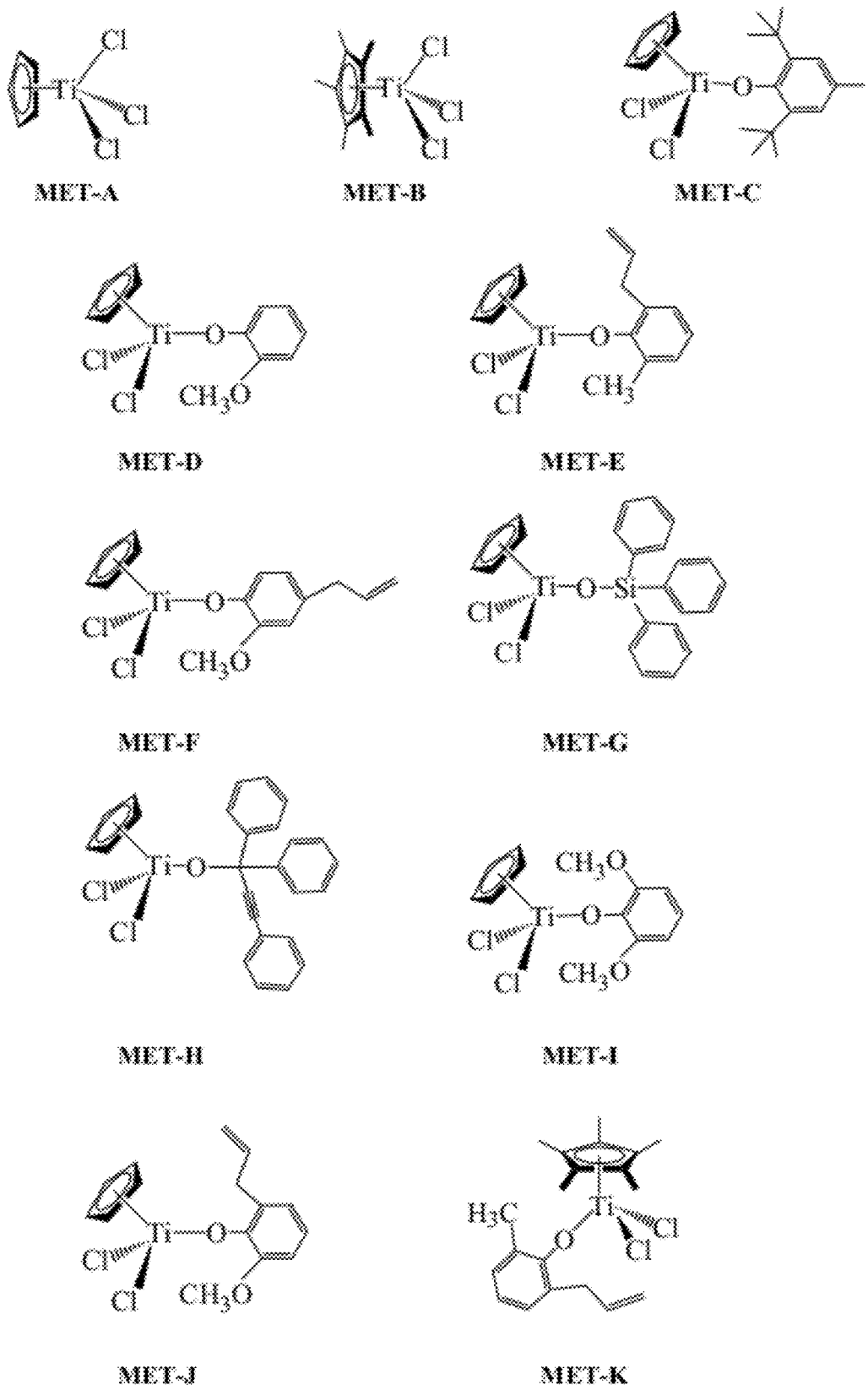
FIG. 1 presents the structures and abbreviations for certain hybrid metallocene or half-metallocene compounds discussed herein.

To define more clearly the terms used herein, the following definitions are provided. To the extent that any definition or usage provided by any document incorporated herein by reference conflicts with the definition or usage provided herein, the definition or usage provided herein controls.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer would be categorized an as ethylene/1-hexene copolymer.

In like manner, the scope of the term "polymerization" includes homopolymerization, copolymerization, terpolymerization, etc. Therefore, a copolymerization process would involve contacting one olefin monomer (e.g., ethylene) and one olefin comonomer (e.g., 1-hexene) to produce a copolymer.

The term "co-catalyst" is used generally herein to refer to organoaluminum compounds that can constitute one component of a catalyst composition. Additionally, "co-catalyst" can refer to other components of a catalyst composition including, but not limited to, aluminoxanes, organoboron or organoborate compounds, and ionizing ionic compounds, as disclosed herein, when used in addition to an activator-support. The term "co-catalyst" is used regardless of the actual function of the compound or any chemical mechanism by which the compound may operate. In one aspect of this invention, the term "co-catalyst" can be used to distinguish that component of the catalyst composition from the hybrid metallocene compound(s).

The terms "chemically-treated solid oxide," "activator-support," "treated solid oxide compound," and the like, are used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide can comprise a calcined contact product of at least one solid oxide with at least one electron-withdrawing anion source compound. Typically, the chemically-treated solid oxide comprises at least one acidic solid oxide compound. The terms "support" and "activator-support" are not used to imply these components are inert, and such components should not be construed as an inert component of the catalyst composition. The activator-support of the present invention can be a chemically-treated solid oxide. The term "activator," as used herein, refers generally to a substance that is capable of converting a metallocene component into a catalyst that can polymerize olefins, or converting a contact product of a metallocene component and a component that provides an activatable ligand (e.g., an alkyl, a hydride) to the metallocene, when the metallocene compound does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The term "fluoroorgano boron compound" is used herein with its ordinary meaning to refer to neutral compounds of the form $BY_3$. The term "fluoroorgano borate compound" also has its usual meaning to refer to the monoanionic salts of a fluoroorgano boron compound of the form $[cation]^+[BY_4]^-$, where Y represents a fluorinated organic group. Materials of these types are generally and collectively referred to as "organoboron or organoborate compounds."

The term "hybrid metallocene," as used herein, describes an unbridged half-metallocene compound with a heteroatom-containing ligand bound to the transition metal. The hybrid metallocenes of this invention contain one $\eta^3$ to $\eta^5$-cyclopentadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this invention comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. In some contexts, the hybrid metallocene may be referred to simply as the "catalyst," in much the same way the term "co-catalyst" may be used herein to refer to, for example, an organoaluminum compound.

The terms "catalyst composition," "catalyst mixture," "catalyst system," and the like, do not depend upon the actual product or composition resulting from the contact or reaction of the initial components of the claimed catalyst composition/mixture/system, the nature of the active catalytic site, or the fate of the co-catalyst, the metallocene compound(s), any olefin monomer used to prepare a precontacted mixture, or the activator (e.g., activator-support), after combining these components. Therefore, the terms "catalyst composition," "catalyst mixture," "catalyst system," and the like, encompass the initial starting components of the composition, as well as whatever products) may result from contacting these initial starting components, and this is inclusive of both heterogeneous and homogenous catalyst systems or compositions.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which may be blended, mixed, slurried, dissolved, reacted, treated, or otherwise contacted in some other manner.

The term "precontacted" mixture is used herein to describe a first mixture of catalyst components that are contacted for a first period of time prior to the first mixture being used to form a "postcontacted" or second mixture of catalyst components that are contacted for a second period of time. Typically, the precontacted mixture can describe a mixture of metallocene compound (one or more than one), olefin monomer (or monomers), and organoaluminum compound (or compounds), before this mixture is contacted with an activator-support(s) and optional additional organoaluminum compound. Thus, precontacted describes components that are used to contact each other, but prior to contacting the components in the second, postcontacted mixture. Accordingly, this invention may occasionally distinguish between a component used to prepare the precontacted mixture and that component after the mixture has been prepared. For example, according to this description, it is possible for the precontacted organoaluminum compound, once it is contacted with the metallocene compound and the olefin monomer, to have reacted to form at least one different chemical compound, formulation, or structure from the distinct organoaluminum compound used to prepare the precontacted mixture. In this case, the precontacted organoaluminum compound or component is described as comprising an organoaluminum compound that was used to prepare the precontacted mixture.

Additionally, the precontacted mixture can describe a mixture of metallocene compound(s) and organoaluminum compound(s), prior to contacting this mixture with an activator-support(s). This precontacted mixture also can describe a mixture of metallocene compound(s), olefin monomer(s), and activator-support(s), before this mixture is contacted with an organoaluminum co-catalyst compound or compounds.

Similarly, the term "postcontacted" mixture is used herein to describe a second mixture of catalyst components that are contacted for a second period of time, and one constituent of which is the "precontacted" or first mixture of catalyst components that were contacted for a first period of time. Typically, the term "postcontacted" mixture is used herein to describe the mixture of metallocene compound(s), olefin monomer(s), organoaluminum compound(s), and activator-support(s) formed from contacting the precontacted mixture of a portion of these components with any additional components added to make up the postcontacted mixture. Often, the activator-support can comprise a chemically-treated solid oxide. For instance, the additional component added to make up the postcontacted mixture can be a chemically-treated solid oxide (one or more than one), and optionally, can include an organoaluminum compound which is the same as or different from the organoaluminum compound used to prepare the precontacted mixture, as described herein. Accordingly, this invention may also occasionally distinguish between a component used to prepare the postcontacted mixture and that component after the mixture has been prepared.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan.

The term "hydrocarbyl" is used herein to specify a hydrocarbon radical group that includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, branched, linear, heteroatom substituted derivatives thereof.

Applicants disclose several types of ranges in the present invention. These include, but are not limited to, a range of number of atoms, a range of integers, a range of weight ratios, a range of molar ratios, a range of molecular weights, a range of temperatures, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_1$ to $C_{18}$ hydrocarbyl group, or in alternative language a hydrocarbyl group having up to 18 carbon atoms, as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the ratio of Mw/Mn provided in one aspect of this invention. By a disclosure that the ratio of Mw/Mn can be in a range from about 3 to about 20, Applicants intend to recite that Mw/Mn can be about 3, about 4, about 5, about 6, about 7, about 8, about 9, about 10, about 11, about 12, about 13, about 14, about 15, about 16, about 17, about 18, about 19, or about 20. Additionally, the Mw/Mn ratio can be within any range from about 3 to about 20 (for example, from about 5 to about 15), and this also includes any combination of ranges between about 3 and about 20 (for example, Mw/Mn can be in a range from about 4 to about 6, or from about 8 to about 13). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The terms "a," "an," "the," etc., are intended to include plural alternatives, e.g., at least one, unless otherwise specified. For instance, the disclosure of "an activator-support" or "a hybrid metallocene compound" is meant to encompass one, or mixtures or combinations of more than one, activator-support or hybrid metallocene compound, respectively.

While compositions and methods are described in terms of "comprising" various components or steps, the compositions and methods can also "consist essentially of" or "consist of" the various components or steps. For example, a catalyst composition of the present invention can comprise; alternatively, can consist essentially of; or alternatively, can consist of: (i) a hybrid metallocene compound and (ii) an activator.

DETAILED DESCRIPTION OF THE INVENTION

The present invention is directed generally to new catalyst compositions, methods for preparing catalyst compositions, methods for using the catalyst compositions to polymerize olefins, the polymer resins produced using such catalyst compositions, and articles produced using these polymer resins. In particular, the present invention relates to half-metallocene compounds with a heteroatom-containing ligand bound to the transition metal, and catalyst compositions employing such hybrid metallocene compounds.

Hybrid Metallocene Compounds

The present invention discloses novel hybrid metallocene compounds having a metallocene moiety and a heteroatom-containing ligand, and methods of making these compounds. For convenience, these compounds will be referred to herein as hybrid metallocene compounds. In one aspect of this invention, the unbridged hybrid metallocene compound can have the formula:

wherein:
M can be Zr, Hf, or Ti;
$X^1$ and $X^2$ independently can be a halide or a substituted or unsubstituted aliphatic, aromatic, or cyclic group, or a combination thereof;
$X^3$ can be a substituted or unsubstituted cyclopentadienyl, indenyl, or fluorenyl group, wherein any substituents on $X^3$ independently can be a hydrogen atom or a substituted or unsubstituted aliphatic, aromatic, or cyclic group, or a combination thereof;
$X^4$ can be —O—$R^A$, —NH—$R^A$, —PH—$R^A$, —S—$R^A$, —O—Si—$R^B{}_3$, or —O—C—$R^B{}_3$; wherein:
  $R^A$ can be an aryl group substituted with a first alkoxy group and a second substituent selected from an alkyl, cycloalkyl, or second alkoxy group, wherein any additional substituents on $R^A$ independently can be a hydrogen atom or an alkyl, cycloalkyl, or alkoxy group; and
  each $R^B$ independently can be a hydrogen atom or a substituted or unsubstituted aliphatic, aromatic, or cyclic group, or a combination thereof.

Unless otherwise specified, formula (I) above, any other structural formulas disclosed herein, and any hybrid metallocene species or compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

The metal in formula (I), M, can be Zr, Hf, or Ti. In one aspect of the present invention, M can be either Zr or Ti, while in another aspect, M can be Ti.

In formula (I), $X^1$ and $X^2$ independently can be a halide, such as a fluorine, chlorine, bromine, or iodine atom. As used herein, an aliphatic group includes linear or branched alkyl and alkenyl groups. Generally, the aliphatic group can contain from 1 to 20 carbon atoms. Unless otherwise specified, alkyl and alkenyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers can include 2-ethyl hexyl and neooctyl. Examples of suitable alkyl groups which can be employed in the present invention can include, but are not limited to, methyl, ethyl, propyl, butyl, pentyl, hexyl, heptyl, octyl, nonyl, or decyl, and the like. Examples of alkenyl groups within the scope of the present invention can include, but are not limited to, ethenyl, propenyl, butenyl, pentenyl, hexenyl, heptenyl, octenyl, nonenyl, decenyl, and the like.

Aromatic groups and combinations with aliphatic groups include aryl and arylalkyl groups, and these can include, but are not limited to, phenyl, alkyl-substituted phenyl, naphthyl, alkyl-substituted naphthyl, phenyl-substituted alkyl, naphthyl-substituted alkyl, and the like. Generally, such groups and combinations of groups can contain less than 20 carbon atoms. Hence, non-limiting examples of such moieties that can be used in the present invention can include phenyl, tolyl, benzyl, dimethylphenyl, trimethylphenyl, phenylethyl, phenylpropyl, phenylbutyl, propyl-2-phenylethyl, and the like. Cyclic groups can include cycloalkyl and cycloalkenyl moieties and such moieties can include, but are not limited to, cyclopentyl, cyclopentenyl, cyclohexyl, cyclohexenyl, and the like. One example of a combination including a cyclic group is a cyclohexylphenyl group. Unless otherwise specified, any substituted aromatic or cyclic moiety used herein is meant to include all regioisomers; for example, the term tolyl is meant to include any possible substituent position, that is, ortho, meta, or para.

In one aspect of the present invention, $X^1$ and $X^2$ independently can be a substituted or unsubstituted aliphatic group having from 1 to 20 carbon atoms. In another aspect, $X^1$ and $X^2$ independently can be methyl, ethyl, propyl, butyl, pentyl, hexyl, heptyl, octyl, nonyl, or decyl. In still another aspect, either $X^1$ or $X^2$, or both, can be trimethylsilylmethyl. In yet another aspect, $X^1$ and $X^2$ independently can be ethenyl, propenyl, butenyl, pentenyl, hexenyl, heptenyl, octenyl, nonenyl, or decenyl. $X^1$ and $X^2$ independently can be a substituted or unsubstituted aromatic group, for example, having up to 20 carbon atoms, in another aspect of the present invention.

In a different aspect, $X^1$ and $X^2$ both can be chlorine atoms. $X^1$ and $X^2$ independently can be phenyl, naphthyl, tolyl, benzyl, dimethylphenyl, trimethylphenyl, phenylethyl, phenylpropyl, phenylbutyl, propyl-2-phenylethyl, cyclopentyl, cyclopentenyl, cyclohexyl, cyclohexenyl, or cyclohexylphenyl in other aspects of this invention. Yet, in another aspect, $X^1$ and $X^2$ independently can be methyl, phenyl, benzyl, or a halide. Further, $X^1$ and $X^2$ independently can be methyl, phenyl, benzyl, or a chlorine atom in another aspect of the present invention.

In formula (I), $X^3$ can be a substituted or unsubstituted cyclopentadienyl, indenyl, or fluorenyl group. In one aspect of the present invention, $X^3$ can be a substituted or unsubstituted cyclopentadienyl group. In another aspect, $X^3$ can be a substituted or unsubstituted indenyl group.

$X^3$ can be an unsubstituted cyclopentadienyl, indenyl, or fluorenyl group. Alternatively, $X^3$ can have one or more substituents. Any substituents on $X^3$ independently can be a hydrogen atom or a substituted or unsubstituted aliphatic, aromatic, or cyclic group, or a combination thereof. Hydrogen is included, therefore the notion of a substituted indenyl and substituted fluorenyl can include partially saturated indenyls and fluorenyls including, but not limited to, tetrahydroindenyls, tetrahydrofluorenyls, and octahydrofluorenyls. Exemplary aliphatics which can be employed in the present invention can include alkyls and alkenyls, examples of which can include, but are not limited to, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, or decenyl, and the like. Illustrate aromatic groups and combinations with aliphatic groups, as discussed above, can include phenyl, tolyl, benzyl, and the like. Cyclic substituents are also contemplated herein, and non-limiting examples were also provided above, including moieties such as cyclopentyl and cyclohexyl.

In one aspect of this invention, each substituent on $X^3$ independently can be a hydrogen atom, or a methyl, ethyl, propyl, n-butyl, t-butyl, or hexyl group. In another aspect, substituents on $X^3$ independently can be ethenyl, propenyl, butenyl, pentenyl, hexenyl, heptenyl, octenyl, nonenyl, decenyl, or a hydrogen atom.

$X^4$ in formula (I) can be —O—$R^A$, —NH—$R^A$, —PH—$R^A$, —S—$R^A$, —O—Si—$R^B_3$, or —O—C—$R^B_3$. In accordance with one aspect of the present invention, $X^4$ can be —O—$R^A$. In accordance with another aspect, $X^4$ can be —NH—$R^A$. In accordance with yet another aspect, $X^4$ can be —PH—$R^A$ or, alternatively, —S—$R^A$. In the —O—$R^A$, —NH—$R^A$, —PH—$R^A$, and —S—$R^A$ moieties, $R^A$ can be an aryl group substituted with a first alkoxy group and a second substituent selected from an alkyl, cycloalkyl, or second alkoxy group. $R^A$ can be an aryl group substituted with a first alkoxy group, and the first alkoxy group can have from 1 to 20 carbons atoms, from 1 to 12 carbon atoms, or from 1 to 8 carbon atoms. Representative alkoxy groups can include, but are not limited to, methoxy, ethoxy, propoxy, butoxy, pentoxy, hexoxy, and the like. Thus, the first alkoxy group on $R^A$ can be a methoxy group, an ethoxy group, a propoxy group, or a butoxy group, for example.

$R^A$ can be substituted with a second substituent selected from an alkyl, cycloalkyl, or second alkoxy group. The alkyl group, cycloalkyl group, and second alkoxy group can be any alkyl group, cycloalkyl group, and alkoxy group disclosed herein. In one aspect, the second substituent on $R^A$ can be a methyl group, an ethyl group, a propyl group, a n-butyl group, a t-butyl group, a cyclopentyl group, a cyclohexyl group, a methoxy group, an ethoxy group, a propoxy group, or a butoxy group; alternatively, a methyl group, an ethyl group, a propyl group, a n-butyl group, or a t-butyl group; alternatively, a cyclopentyl group or a cyclohexyl group; or alternatively, a methoxy group, an ethoxy group, a propoxy group, or a butoxy group.

In an aspect of this invention, $R^A$ can be a disubstituted aryl group, and in a further aspect, $R^A$ can be a 2,6-disubstituted aryl group. In other aspects, $R^A$ can be further substituted with additional substituents; generally, such additional substituents independently can be a hydrogen atom or an alkyl, cycloalkyl, or alkoxy group.

In certain aspects, $X^4$ can be —O—$R^A$. Non-limiting examples of $X^4$ in these aspects of the invention can include, but are not limited to, the following moieties:

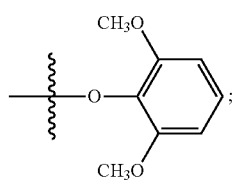

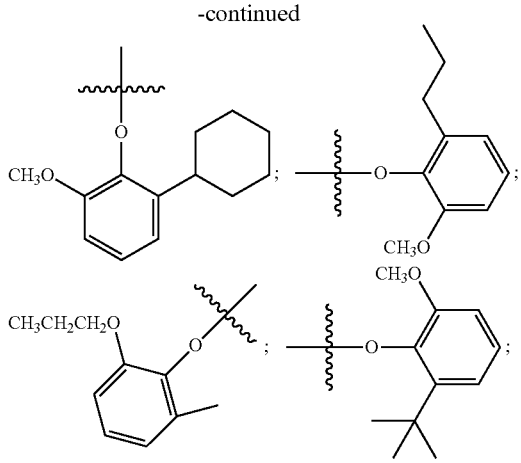

and the like.

In accordance with other aspects of the invention, $X^4$ in formula (I) can be —O—Si—$R^B{}_3$ or —O—C—$R^B{}_3$; alternatively, $X^4$ can be —O—Si—$R^B{}_3$; or alternatively, $X^4$ can be —O—C—$R^B{}_3$. Each $R^B$ independently can be a hydrogen atom or a substituted or unsubstituted aliphatic, aromatic, or cyclic group, or a combination thereof. Each $R^B$, therefore, can be the same or different. Exemplary aliphatic, aromatic, or cyclic groups, or combinations thereof, which can be employed as $R^B$, independently, can include, but are not limited to, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, xylyl, methyl benzyl, 1-ethenyl-2-phenyl, 1-ethynyl-2-phenyl, cyclopentyl, cyclohexyl, and the like.

In an aspect, $X^4$ in formula (I) can be —O—Si—$R^B{}_3$ or —O—C—$R^B{}_3$, and each $R^B$ independently can be a hydrogen atom, a methyl group, an ethyl group, a propyl group, a n-butyl group, a t-butyl group, a phenyl group, a benzyl group, a tolyl group, a xylyl group, a methyl benzyl group, a 1-ethenyl-2-phenyl group, or a 1-ethynyl-2-phenyl group. In another aspect, each $R^B$ independently can be a methyl group, an ethyl group, a propyl group, a n-butyl group, a t-butyl group, a phenyl group, a benzyl group, a tolyl group, a xylyl group, a methyl benzyl group, a 1-ethenyl-2-phenyl group, or a 1-ethynyl-2-phenyl group. Yet, in another aspect, each $R^B$ independently can be a phenyl group, a benzyl group, a tolyl group, a xylyl group, a methyl benzyl group, a 1-ethenyl-2-phenyl group, or a 1-ethynyl-2-phenyl group. Additionally, $X^4$ in formula (I) can be —O—Si—$R^B{}_3$ or —O—C—$R^B{}_3$, and each $R^B$ independently can be a phenyl group, a benzyl group, a methyl benzyl group, a 1-ethenyl-2-phenyl group, or a 1-ethynyl-2-phenyl group, in a particular aspect of this invention.

In formula (I), substituted aliphatic, aromatic, or cyclic groups, and combinations thereof, are disclosed. Such groups described herein are intended to include substituted analogs with substitutions at any position on these groups that conform to the normal rules of chemical valence. Thus, groups substituted with one or more than one substituent are contemplated.

Such substituents, when present, can be independently selected from an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted derivative thereof, any of which having from 1 to about 20 carbon atoms; a halide; or hydrogen; as long as these groups do not terminate the activity of the catalyst composition. Examples of each of these substituent groups can include, but are not limited to, the following groups.

Examples of halide substituents, in each occurrence, can include fluoride, chloride, bromide, and iodide.

In each occurrence, oxygen groups are oxygen-containing groups, examples of which can include, but are not limited to, alkoxy or aryloxy groups (—$OR^X$), —$OSiR^X{}_3$, —$OPR^X{}_2$, —$OAlR^X{}_2$, and the like, including substituted derivatives thereof, wherein $R^X$ in each occurrence can be alkyl, cycloalkyl, aryl, aralkyl, substituted alkyl, substituted aryl, or substituted aralkyl having from 1 to 20 carbon atoms. Examples of alkoxy or aryloxy groups (—$OR^X$) groups can include, but are not limited to, methoxy, ethoxy, propoxy, butoxy, phenoxy, substituted phenoxy, and the like.

In each occurrence, sulfur groups are sulfur-containing groups, examples of which can include, but are not limited to, —$SR^X$ and the like, including substituted derivatives thereof, wherein $R^X$ in each occurrence can be alkyl, cycloalkyl, aryl, aralkyl, substituted alkyl, substituted aryl, or substituted aralkyl having from 1 to 20 carbon atoms.

In each occurrence, nitrogen groups are nitrogen-containing groups, which can include, but are not limited to, —$NR^X{}_2$ and the like, including substituted derivatives thereof, wherein $R^X$ in each occurrence can be alkyl, cycloalkyl, aryl, aralkyl, substituted alkyl, substituted aryl, or substituted aralkyl having from 1 to 20 carbon atoms.

In each occurrence, phosphorus groups are phosphorus-containing groups, which can include, but are not limited to, —$PR^X{}_2$, —$P(OR^X)_2$, and the like, including substituted derivatives thereof, wherein $R^X$ in each occurrence can be alkyl, cycloalkyl, aryl, aralkyl, substituted alkyl, substituted aryl, or substituted aralkyl having from 1 to 20 carbon atoms.

In each occurrence, arsenic groups are arsenic-containing groups, which can include, but are not limited to, —$AsR^X{}_2$, —$As(OR^X)_2$, and the like, including substituted derivatives thereof, wherein $R^X$ in each occurrence can be alkyl, cycloalkyl, aryl, aralkyl, substituted alkyl, substituted aryl, or substituted aralkyl having from 1 to 20 carbon atoms.

In each occurrence, carbon groups are carbon-containing groups, which can include, but are not limited to, alkyl halide groups that comprise halide-substituted alkyl groups with 1 to 20 carbon atoms, aralkyl groups with 1 to 20 carbon atoms, —$C(NR^X)H$, —$C(NR^X)R^X$, —$C(NR^X)OR^X$, and the like, including substituted derivatives thereof, wherein $R^X$ in each occurrence can be alkyl, cycloalkyl, aryl, aralkyl, substituted alkyl, substituted aryl, or substituted aralkyl having from 1 to 20 carbon atoms.

In each occurrence, silicon groups are silicon-containing groups, which can include, but are not limited to, silyl groups such as alkylsilyl groups, arylsilyl groups, arylalkylsilyl groups, siloxy groups, and the like, which in each occurrence can have from 1 to 20 carbon atoms. For example, silicon group substituents can include trimethylsilyl and phenyloctylsilyl groups.

In each occurrence, germanium groups are germanium-containing groups, which can include, but are not limited to, germyl groups such as alkylgermyl groups, arylgermyl groups, arylalkylgermyl groups, germyloxy groups, and the like, which in each occurrence can have from 1 to 20 carbon atoms.

In each occurrence, tin groups are tin-containing groups, which can include, but are not limited to, stannyl groups such as alkylstannyl groups, arylstannyl groups, arylalkylstannyl groups, stannoxy (or "stannyloxy") groups, and the like, which in each occurrence can have from 1 to 20 carbon atoms. Thus, tin groups can include, but are not limited to, stannoxy groups.

In each occurrence, lead groups are lead-containing groups, which can include, but are not limited to, alkyllead groups, aryllead groups, arylalkyllead groups, and the like, which in each occurrence, can have from 1 to 20 carbon atoms.

In each occurrence, boron groups are boron-containing groups, which can include, but are not limited to, —BR$^X{}_2$, —BX$_2$, —BR$^X$X, and the like, wherein X can be a monoanionic group such as hydride, alkoxide, alkyl thiolate, and the like, and wherein R$^X$ in each occurrence can be alkyl, cycloalkyl, aryl, aralkyl, substituted alkyl, substituted aryl, or substituted aralkyl having from 1 to 20 carbon atoms.

In each occurrence, aluminum groups are aluminum-containing groups, which can include, but are not limited to, —AlR$^X$, —AlX$_2$, —AlR$^X$X, wherein X can be a monoanionic group such as hydride, alkoxide, alkyl thiolate, and the like, and wherein R$^X$ in each occurrence can be alkyl, cycloalkyl, aryl, aralkyl, substituted alkyl, substituted aryl, or substituted aralkyl having from 1 to 20 carbon atoms.

Examples of inorganic groups that may be used as substituents, in each occurrence can include, but are not limited to, —OAlX$_2$, —OSiX$_3$, —OPX$_2$, —SX, —AsX$_2$, —PX$_2$, and the like, wherein X can be a monoanionic group such as hydride, amide, alkoxide, alkyl thiolate, and the like, and wherein any alkyl, cycloalkyl, aryl, aralkyl, substituted alkyl, substituted aryl, or substituted aralkyl group or substituent on these ligands can have from 1 to 20 carbon atoms.

Examples of organometallic groups that may be used as substituents, in each occurrence, can include, but are not limited to, organoboron groups, organoaluminum groups, organogallium groups, organosilicon groups, organogermanium groups, organotin groups, organolead groups, organotransition metal groups, and the like, having from 1 to 20 carbon atoms.

In accordance with one aspect of the present invention, M can be Zr or Ti in formula (I), and X$^1$ and X$^2$ independently can be a methyl group, a phenyl group, a benzyl group, or a halide. In this aspect, X$^3$ can be a substituted or unsubstituted cyclopentadienyl group, and X$^4$ can be —O—R$^A$. In these and other aspects, R$^A$ can be a disubstituted aryl group (e.g., a 2,6-disubstituted aryl group), one substituent of which can be a methoxy group, an ethoxy group, a propoxy group, or a butoxy group; and the other substituent of which can be a methyl group, an ethyl group, a propyl group, a n-butyl group, a t-butyl group, a cyclopentyl group, a cyclohexyl group, a methoxy group, an ethoxy group, a propoxy group, or a butoxy group.

In accordance with another aspect, M can be Zr or Ti in formula (I), and X$^1$ and X$^2$ independently can be a methyl group, a phenyl group, a benzyl group, or a halide. In this aspect, X$^3$ can be a substituted or unsubstituted cyclopentadienyl group, and X$^4$ can be —O—Si—R$^B{}_3$ or —O—C—R$^B{}_3$. In these and other aspects, each R$^B$ independently can a methyl group, an ethyl group, a propyl group, a n-butyl group, a t-butyl group, a phenyl group, a benzyl group, a tolyl group, a xylyl group, a methyl benzyl group, a 1-ethenyl-2-phenyl group, or a 1-ethynyl-2-phenyl group; alternatively, each R$^B$ independently can be a phenyl group, a benzyl group, a tolyl group, a xylyl group, a methyl benzyl group, a 1-ethenyl-2-phenyl group, or a 1-ethynyl-2-phenyl group.

In accordance with another aspect, hybrid metallocene compounds disclosed herein can have the formula:

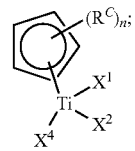

(II)

wherein:
X$^1$ and X$^2$ independently can be a methyl group, a phenyl group, a benzyl group, or a halide;
each R$^C$ independently can be a hydrogen atom, a methyl group, an ethyl group, a propyl group, a n-butyl group, a t-butyl group, or a hexyl group;
n can be an integer from 0 to 5, inclusive;
X$^4$ can be —O—R$^A$, —O—Si—R$^B{}_3$, or —O—C—R$^B{}_3$;
wherein:
R$^A$ can be a 2,6-disubstituted aryl group, wherein the substituent at the 2-position can be a methoxy group, an ethoxy group, a propoxy group, or a butoxy group, and the substituent at the 6-position can be a methyl group, an ethyl group, a propyl group, a n-butyl group, a t-butyl group, a cyclopentyl group, a cyclohexyl group, a methoxy group, an ethoxy group, a propoxy group, or a butoxy group; and
each R$^B$ independently can be a phenyl group, a benzyl group, a tolyl group, a xylyl group, a methyl benzyl group, a 1-ethenyl-2-phenyl group, or a 1-ethynyl-2-phenyl group.

Yet, in accordance with another aspect, hybrid metallocene compounds disclosed herein can have the formula:

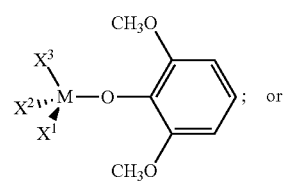

(III)

or

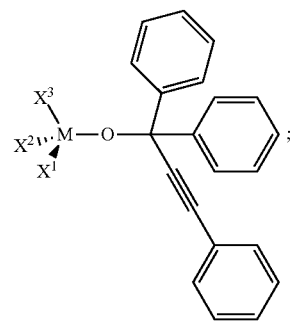

(IV)

wherein:
each M independently can be Zr, Hf, or Ti;
each X$^1$ and X$^2$ independently can be a halide or a substituted or unsubstituted aliphatic, aromatic, or cyclic group, or a combination thereof;
each X$^3$ independently can be a substituted or unsubstituted cyclopentadienyl, indenyl, or fluorenyl group, wherein any substituents on X$^3$ independently can be a hydrogen atom or a substituted or unsubstituted aliphatic, aromatic, or cyclic group, or a combination thereof.

In particular aspects contemplated herein, M in formulas (III) and (IV) can be either Zr or Ti, or alternatively, M can be Ti. Each $X^1$ and $X^2$ independently can be any halide or any substituted or unsubstituted aliphatic, aromatic, or cyclic group, or combination of groups, disclosed herein. For instance, each $X^1$ and $X^2$ independently can be a methyl group, a phenyl group, a benzyl group, or a halide. Additionally, each $X^3$ independently can be a substituted or unsubstituted indenyl group or, alternatively, each $X^3$ independently can be a substituted or unsubstituted cyclopentadienyl group. In some aspects, $X^3$ can be unsubstituted (e.g., an unsubstituted cyclopentadienyl group), while in other aspects, $X^3$ can have one or more substituents. Any substituents on $X^3$ independently can be a hydrogen atom or any substituted or unsubstituted aliphatic, aromatic, or cyclic group, or combination of groups, disclosed herein. As an example, each substituent on each $X^3$ independently can be a hydrogen atom, or a methyl, ethyl, propyl, n-butyl, t-butyl, or hexyl group.

Illustrative and non-limiting examples of hybrid metallocene compounds of the present invention can include the following compounds:

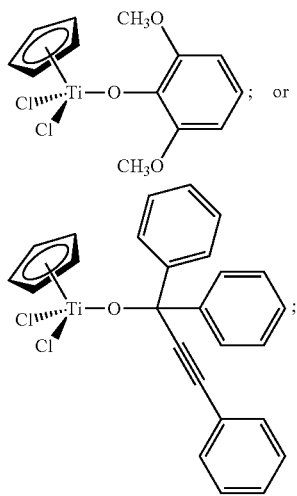

and the like.

Other hybrid metallocene compounds are contemplated as being suitable for use in the present invention, therefore, the scope of the present invention is not limited to the hybrid metallocene species provided above.

Methods of making hybrid metallocene compounds of the present invention also are provided. In addition to the procedures employed in the Examples that follow, suitable methods can include those described in Scholz et al., *Journal of Organometallic Chemistry* (1993), 443(1), 93-9; Thorn et al., *Journal of the Chemical Society, Dalton Transactions* (2002), 17, 3398-3405; and U.S. Patent Publication No. 2010-0010174; the disclosures of which are incorporated herein by reference in their entirety.

Activator-Support

The present invention encompasses various catalyst compositions containing an activator, which can be an activator-support. In one aspect, the activator-support can comprise a chemically-treated solid oxide. Alternatively, the activator-support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or combinations thereof.

Generally, chemically-treated solid oxides exhibit enhanced acidity as compared to the corresponding untreated solid oxide compound. The chemically-treated solid oxide also can function as a catalyst activator as compared to the corresponding untreated solid oxide. While the chemically-treated solid oxide can activate the hybrid metallocene in the absence of co-catalysts, it is not necessary to eliminate co-catalysts from the catalyst composition. The activation function of the activator-support may be evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron or organoborate compounds, ionizing ionic compounds, and the like.

The chemically-treated solid oxide can comprise a solid oxide treated with an electron-withdrawing anion. While not intending to be bound by the following statement, it is believed that treatment of the solid oxide with an electron-withdrawing component augments or enhances the acidity of the oxide. Thus, either the activator-support exhibits Lewis or Brønsted acidity that is typically greater than the Lewis or Brønsted acid strength of the untreated solid oxide, or the activator-support has a greater number of acid sites than the untreated solid oxide, or both. One method to quantify the acidity of the chemically-treated and untreated solid oxide materials can be by comparing the polymerization activities of the treated and untreated oxides under acid catalyzed reactions.

Chemically-treated solid oxides of this invention generally can be formed from an inorganic solid oxide that exhibits Lewis acidic or Brønsted acidic behavior and has a relatively high porosity. The solid oxide can be chemically-treated with an electron-withdrawing component, typically an electron-withdrawing anion, to form an activator-support.

According to one aspect of the present invention, the solid oxide used to prepare the chemically-treated solid oxide can have a pore volume greater than about 0.1 cc/g. According to another aspect of the present invention, the solid oxide can have a pore volume greater than about 0.5 cc/g. According to yet another aspect of the present invention, the solid oxide can have a pore volume greater than about 1.0 cc/g.

In another aspect, the solid oxide can have a surface area of from about 100 to about 1000 m²/g. In yet another aspect, the solid oxide can have a surface area of from about 200 to about 800 m²/g. In still another aspect of the present invention, the solid oxide can have a surface area of from about 250 to about 600 m²/g.

The chemically-treated solid oxide can comprise a solid inorganic oxide comprising oxygen and one or more elements selected from Group 2, 3, 4, 5, 6, 7, 8, 9, 10, 11, 12, 13, 14, or 15 of the periodic table, or comprising oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used to form the chemically-treated solid oxide can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide can comprise silica, alumina, silica-alumina, silica-coated alumina, aluminum phosphate, aluminophosphate, heteropolytungstate, titania, zirconia, magnesia, boria, zinc oxide, mixed oxides thereof, or any combination thereof.

The solid oxide of this invention encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present invention, either singly or in combination, can include, but are not limited to, silica-alumina, silica-titania, silica-zirconia, zeolites, various clay minerals, alumina-titania, alumina-zirconia, zinc-aluminate, alumina-boria, silica-boria, aluminophosphate-silica, titania-zirconia, and the like. The solid oxide of this invention also encompasses oxide materials such as silica-coated alumina, as described in U.S. Patent Publication No. 2010-0076167, the disclosure of which is incorporated herein by reference in its entirety.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present invention, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, and the like, including mixtures and combinations thereof. In addition, other ionic or non-ionic compounds that serve as sources for these electron-withdrawing anions also can be employed in the present invention. It is contemplated that the electron-withdrawing anion can be, or can comprise, fluoride, chloride, bromide, phosphate, triflate, bisulfate, or sulfate, and the like, or any combination thereof, in some aspects of this invention. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof.

Thus, for example, the activator-support (e.g., chemically-treated solid oxide) used in the catalyst compositions of the present invention can be, or can comprise, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In one aspect, the activator-support can be, or can comprise, fluorided alumina, sulfated alumina, fluorided silica-alumina, sulfated silica-alumina, fluorided silica-coated alumina, sulfated silica-coated alumina, phosphated silica-coated alumina, and the like, or any combination thereof. In another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; or alternatively, fluorided silica-coated alumina.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion can include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion can include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the activator-support to the desired level. Combinations of electron-withdrawing components can be contacted with the oxide material simultaneously or individually, and in any order that affords the desired chemically-treated solid oxide acidity. For example, one aspect of this invention can employ two or more electron-withdrawing anion source compounds in two or more separate contacting steps.

Thus, a process by which a chemically-treated solid oxide can be prepared is as follows: a selected solid oxide, or combination of solid oxides, can be contacted with a first electron-withdrawing anion source compound to form a first mixture; this first mixture can be calcined and then contacted with a second electron-withdrawing anion source compound to form a second mixture; the second mixture then can be calcined to form a treated solid oxide. In such a process, the first and second electron-withdrawing anion source compounds can be either the same or different compounds.

According to another aspect of the present invention, the chemically-treated solid oxide can comprise a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. Non-limiting examples of the metal or metal ion can include zinc, nickel, vanadium, titanium, silver, copper, gallium, tin, tungsten, molybdenum, zirconium, and the like, or combinations thereof. Examples of chemically-treated solid oxides that contain a metal or metal ion can include, but are not limited to, chlorided zinc-impregnated alumina, fluorided titanium-impregnated alumina, fluorided zinc-impregnated alumina, chlorided zinc-impregnated silica-alumina, fluorided zinc-impregnated silica-alumina, sulfated zinc-impregnated alumina, chlorided zinc aluminate, fluorided zinc aluminate, sulfated zinc aluminate, silica-coated alumina treated with hexafluorotitanic acid, silica-coated alumina treated with zinc and then fluorided, and the like, or any combination thereof.

Any method of impregnating the solid oxide material with a metal can be used. The method by which the oxide is contacted with a metal source, typically a salt or metal-containing compound, can include, but is not limited to, gelling, co-gelling, impregnation of one compound onto another, and the like. If desired, the metal-containing compound can be added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, and the like, or combinations of these metals. For example, zinc often can be used to impregnate the solid oxide because it can provide improved catalyst activity at a low cost.

The solid oxide can be treated with metal salts or metal-containing compounds before, after, or at the same time that the solid oxide is treated with the electron-withdrawing anion. Following any contacting method, the contacted mixture of solid compound, electron-withdrawing anion, and the metal ion can be calcined. Alternatively, a solid oxide material, an electron-withdrawing anion source, and the metal salt or metal-containing compound can be contacted and calcined simultaneously.

Various processes can be used to form the chemically-treated solid oxide useful in the present invention. The chemically-treated solid oxide can comprise the contact product of one or more solid oxides with one or more electron-withdrawing anion sources. It is not required that the solid oxide be calcined prior to contacting the electron-withdrawing anion source. Typically, the contact product can be calcined either during or after the solid oxide is contacted with the electron-withdrawing anion source. The solid oxide can be calcined or uncalcined. Various processes to prepare solid oxide activator-supports that can be employed in this invention have been reported. For example, such methods are described in U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, and 6,750,302, the disclosures of which are incorporated herein by reference in their entirety.

According to one aspect of the present invention, the solid oxide material can be chemically-treated by contacting it with an electron-withdrawing component, typically an electron-withdrawing anion source. Further, the solid oxide material optionally can be chemically treated with a metal ion, and then calcined to form a metal-containing or metal-impregnated chemically-treated solid oxide. According to another aspect of the present invention, the solid oxide material and electron-withdrawing anion source can be contacted and calcined simultaneously.

The method by which the oxide is contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide, electron-withdrawing anion, and optional metal ion, can be calcined.

The solid oxide activator-support (i.e., chemically-treated solid oxide) thus can be produced by a process comprising:

1) contacting a solid oxide (or solid oxides) with an electron-withdrawing anion source compound (or compounds) to form a first mixture; and 2) calcining the first mixture to form the solid oxide activator-support.

According to another aspect of the present invention, the solid oxide activator-support (chemically-treated solid oxide) can be produced by a process comprising:

1) contacting a solid oxide (or solid oxides) with a first electron-withdrawing anion source compound to form a first mixture;

2) calcining the first mixture to produce a calcined first mixture;

3) contacting the calcined first mixture with a second electron-withdrawing anion source compound to form a second mixture; and 4) calcining the second mixture to form the solid oxide activator-support.

According to yet another aspect of the present invention, the chemically-treated solid oxide can be produced or formed by contacting the solid oxide with the electron-withdrawing anion source compound, where the solid oxide compound is calcined before, during, or after contacting the electron-withdrawing anion source, and where there is a substantial absence of aluminoxanes, organoboron or organoborate compounds, and ionizing ionic compounds.

Calcining of the treated solid oxide generally can be conducted in an ambient atmosphere, typically in a dry ambient atmosphere, at a temperature from about 200° C. to about 900° C., and for a time of about 1 minute to about 100 hours. Calcining can be conducted at a temperature of from about 300° C. to about 800° C., or alternatively, at a temperature of from about 400° C. to about 700° C. Calcining can be conducted for about 30 minutes to about 50 hours, or for about 1 hour to about 15 hours. Thus, for example, calcining can be carried out for about 1 to about 10 hours at a temperature of from about 350° C. to about 550° C. Any suitable ambient atmosphere can be employed during calcining. Generally, calcining can be conducted in an oxidizing atmosphere, such as air. Alternatively, an inert atmosphere, such as nitrogen or argon, or a reducing atmosphere, such as hydrogen or carbon monoxide, can be used.

According to one aspect of the present invention, the solid oxide material can be treated with a source of halide ion, sulfate ion, or a combination of anions, optionally treated with a metal ion, and then calcined to provide the chemically-treated solid oxide in the form of a particulate solid. For example, the solid oxide material can be treated with a source of sulfate (termed a "sulfating agent"), a source of chloride ion (termed a "chloriding agent"), a source of fluoride ion (termed a "fluoriding agent"), or a combination thereof, and calcined to provide the solid oxide activator. Useful acidic activator-supports can include, but are not limited to, bromided alumina, chlorided alumina, fluorided alumina, sulfated alumina, bromided silica-alumina, chlorided silica-alumina, fluorided silica-alumina, sulfated silica-alumina, bromided silica-zirconia, chlorided silica-zirconia, fluorided silica-zirconia, sulfated silica-zirconia, fluorided silica-titania, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator-supports optionally can be treated or impregnated with a metal ion.

The chemically-treated solid oxide can comprise a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension. Examples of suitable fluoriding agents can include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), hexafluorotitanic acid ($H_2TiF_6$), ammonium hexafluorotitanic acid (($NH_4)_2TiF_6$), hexafluorozirconic acid ($H_2ZrF_6$), $AlF_3$, $NH_4AlF_4$, analogs thereof, and combinations thereof. Triflic acid and ammonium triflate also can be employed. For example, ammonium bifluoride ($NH_4HF_2$) can be used as the fluoriding agent, due to its ease of use and availability.

If desired, the solid oxide can be treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this aspect of the invention can include, but are not limited to, freons, perfluorohexane, perfluorobenzene, fluoromethane, trifluoroethanol, and the like, and combinations thereof. Calcining temperatures generally must be high enough to decompose the compound and release fluoride. Gaseous hydrogen fluoride (HF) or fluorine ($F_2$) itself also can be used with the solid oxide if fluorided while calcining. Silicon tetrafluoride ($SiF_4$) and compounds containing tetrafluoroborate ($BF_4^-$) also can be employed. One convenient method of contacting the solid oxide with the fluoriding agent can be to vaporize a fluoriding agent into a gas stream used to fluidize the solid oxide during calcination.

Similarly, in another aspect of this invention, the chemically-treated solid oxide can comprise a chlorided solid oxide in the form of a particulate solid. The chlorided solid oxide can be formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used, such as $SiCl_4$, $SiMe_2Cl_2$, $TiCl_4$, $BCl_3$, and the like, including mixtures thereof. Volatile organic chloriding agents can be used. Examples of suitable volatile organic chloriding agents can include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcining. One convenient method of contacting the oxide with the chloriding agent can be to vaporize a chloriding agent into a gas stream used to fluidize the solid oxide during calcination.

The amount of fluoride or chloride ion present before calcining the solid oxide generally can be from about 1 to about 50% by weight, where the weight percent is based on the weight of the solid oxide, for example, silica-alumina, before calcining According to another aspect of this invention, the amount of fluoride or chloride ion present before calcining the solid oxide can be from about 1 to about 25% by weight, and according to another aspect of this invention, from about 2 to about 20% by weight. According to yet another aspect of this invention, the amount of fluoride or chloride ion present before calcining the solid oxide can be from about 4 to about 10% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically can have a pore volume greater than about 0.5 cc/g. According to one aspect of the present invention, the pore volume can be greater than about 0.8 cc/g, and according to another aspect of the present invention, greater than about 1.0 cc/g. Further, the silica-alumina generally can have a surface area greater than about 100 $m^2/g$. According to another aspect of this invention, the surface area can be greater than about 250 $m^2/g$. Yet, in another aspect, the surface area can be greater than about 350 $m^2/g$.

The silica-alumina utilized in the present invention typically can have an alumina content from about 5 to about 95% by weight. According to one aspect of this invention, the alumina content of the silica-alumina can be from about 5 to about 50%, or from about 8% to about 30%, alumina by weight. In another aspect, high alumina content silica-alumina compounds can be employed, in which the alumina content of these silica-alumina compounds typically ranges from about 60% to about 90%, or from about 65% to about 80%, alumina by weight. According to yet another aspect of this invention, the solid oxide component can comprise alumina without silica, and according to another aspect of this invention, the solid oxide component can comprise silica without alumina.

The sulfated solid oxide can comprise sulfate and a solid oxide component, such as alumina or silica-alumina, in the form of a particulate solid. Optionally, the sulfated oxide can be treated further with a metal ion such that the calcined sulfated oxide comprises a metal. According to one aspect of the present invention, the sulfated solid oxide can comprise sulfate and alumina. In some instances, the sulfated alumina can be formed by a process wherein the alumina is treated with a sulfate source, for example, sulfuric acid or a sulfate salt such as ammonium sulfate. This process generally can be performed by forming a slurry of the alumina in a suitable solvent, such as alcohol or water, in which the desired concentration of the sulfating agent has been added. Suitable organic solvents can include, but are not limited to, the one to three carbon alcohols because of their volatility and low surface tension.

According to one aspect of this invention, the amount of sulfate ion present before calcining can be from about 0.5 to about 100 parts by weight sulfate ion to about 100 parts by weight solid oxide. According to another aspect of this invention, the amount of sulfate ion present before calcining can be from about 1 to about 50 parts by weight sulfate ion to about 100 parts by weight solid oxide, and according to still another aspect of this invention, from about 5 to about 30 parts by weight sulfate ion to about 100 parts by weight solid oxide. These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

According to another aspect of the present invention, the activator-support used in preparing the catalyst compositions of this invention can comprise an ion-exchangeable activator-support including, but not limited to, silicate and aluminosilicate compounds or minerals, either with layered or non-layered structures, and combinations thereof. In another aspect of this invention, ion-exchangeable, layered aluminosilicates such as pillared clays can be used as activator-supports. When the acidic activator-support comprises an ion-exchangeable activator-support, it can optionally be treated with at least one electron-withdrawing anion such as those disclosed herein, though typically the ion-exchangeable activator-support is not treated with an electron-withdrawing anion.

According to another aspect of the present invention, the activator-support of this invention can comprise clay minerals having exchangeable cations and layers capable of expanding. Typical clay mineral activator-supports can include, but are not limited to, ion-exchangeable, layered aluminosilicates such as pillared clays. Although the term "support" is used, it is not meant to be construed as an inert component of the catalyst composition, but rather can be considered an active part of the catalyst composition, because of its intimate association with the hybrid metallocene component.

According to another aspect of the present invention, the clay materials of this invention can encompass materials either in their natural state or that have been treated with various ions by wetting, ion exchange, or pillaring. Typically, the clay material activator-support of this invention can comprise clays that have been ion exchanged with large cations, including polynuclear, highly charged metal complex cations. However, the clay material activator-supports of this invention also can encompass clays that have been ion exchanged with simple salts, including, but not limited to, salts of Al(III), Fe(II), Fe(III), and Zn(II) with ligands such as halide, acetate, sulfate, nitrate, or nitrite.

According to another aspect of the present invention, the activator-support can comprise a pillared clay. The term "pillared clay" is used to refer to clay materials that have been ion exchanged with large, typically polynuclear, highly charged metal complex cations. Examples of such ions can include, but are not limited to, Keggin ions which can have charges such as 7+, various polyoxometallates, and other large ions. Thus, the term pillaring can refer to a simple exchange reaction in which the exchangeable cations of a clay material are replaced with large, highly charged ions, such as Keggin ions. These polymeric cations then can be immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure can be maintained and the porosity can be enhanced. The resulting pores can vary in shape and size as a function of the pillaring material and the parent clay material used. Examples of pillaring and pillared clays are found in: T. J. Pinnavaia, *Science* 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. No. 4,452,910; U.S. Pat. No. 5,376,611; and U.S. Pat. No. 4,060,480; the disclosures of which are incorporated herein by reference in their entirety.

The pillaring process can utilize clay minerals having exchangeable cations and layers capable of expanding. Any pillared clay that can enhance the polymerization of olefins in the catalyst composition of the present invention can be used. Therefore, suitable clay minerals for pillaring can include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites; mixed-layer clays; the fibrous clays including but not limited to sepiolites, attapulgites, and palygorskites; a serpentine clay; illite; laponite; saponite; and any combination thereof. In one aspect, the pillared clay activator-support can comprise bentonite or montmorillonite. The principal component of bentonite is montmorillonite.

The pillared clay can be pretreated if desired. For example, a pillared bentonite can be pretreated by drying at about 300° C. under an inert atmosphere, typically dry nitrogen, for about 3 hours, before being added to the polymerization reactor. Although an exemplary pretreatment is described herein, it should be understood that the preheating can be carried out at many other temperatures and times, including any combination of temperature and time steps, all of which are encompassed by this invention.

The activator-support used to prepare the catalyst compositions of the present invention can be combined with other inorganic support materials, including, but not limited to, zeolites, inorganic oxides, phosphated inorganic oxides, and the like. In one aspect, typical support materials that can be used include, but are not limited to, silica, silica-alumina, alumina, titania, zirconia, magnesia, boria, thoria, aluminophosphate, aluminum phosphate, silica-titania, coprecipitated silica/titania, mixtures thereof, or any combination thereof.

According to another aspect of the present invention, one or more of the hybrid metallocene compounds can be precontacted with an olefin monomer and an organoaluminum compound for a first period of time prior to contacting this mixture with the activator-support. Once the precontacted mixture of the metallocene compound(s), olefin monomer, and organoaluminum compound is contacted with the activator-support, the composition further comprising the activator-support is termed a "postcontacted" mixture. The postcontacted mixture can be allowed to remain in further contact for a second period of time prior to being charged into the reactor in which the polymerization process will be carried out.

According to yet another aspect of the present invention, one or more of the hybrid metallocene compounds can be precontacted with an olefin monomer and an activator-support for a first period of time prior to contacting this mixture with the organoaluminum compound. Once the precontacted mixture of the metallocene compound(s), olefin monomer, and activator-support is contacted with the organoaluminum compound, the composition further comprising the organoaluminum is termed a "postcontacted" mixture. The postcontacted mixture can be allowed to remain in further contact for a second period of time prior to being introduced into the polymerization reactor.

Organoaluminum Compounds

In some aspects, catalyst compositions of the present invention can comprise one or more organoaluminum compounds. Such compounds can include, but are not limited to, compounds having the formula:

$$(R^1)_3Al;$$

where $R^1$ can be an aliphatic group having from 1 to 10 carbon atoms. For example, $R^1$ can be methyl, ethyl, propyl, butyl, hexyl, or isobutyl.

Other organoaluminum compounds which can be used in catalyst compositions disclosed herein can include, but are not limited to, compounds having the formula:

$$Al(X^5)_m(X^6)_{3-m},$$

where $X^5$ can be a hydrocarbyl; $X^6$ can be an alkoxide or an aryloxide, a halide, or a hydride; and m can be from 1 to 3, inclusive. Hydrocarbyl is used herein to specify a hydrocarbon radical group and includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, branched, linear, and/or heteroatom substituted derivatives thereof.

In one aspect, $X^5$ can be a hydrocarbyl having from 1 to about 18 carbon atoms. In another aspect of the present invention, $X^5$ can be an alkyl having from 1 to 10 carbon atoms. For example, $X^5$ can be methyl, ethyl, propyl, n-butyl, sec-butyl, isobutyl, or hexyl, and the like, in yet another aspect of the present invention.

According to one aspect of the present invention, $X^6$ can be an alkoxide or an aryloxide, any one of which has from 1 to 18 carbon atoms, a halide, or a hydride. In another aspect of the present invention, $X^6$ can be selected independently from fluorine and chlorine. Yet, in another aspect, $X^6$ can be chlorine.

In the formula, $Al(X^5)_m(X^6)_{3-m}$, m can be a number from 1 to 3, inclusive, and typically, m can be 3. The value of m is not restricted to be an integer; therefore, this formula can include sesquihalide compounds or other organoaluminum cluster compounds.

Examples of organoaluminum compounds suitable for use in accordance with the present invention can include, but are not limited to, trialkylaluminum compounds, dialkylaluminum halide compounds, dialkylaluminum alkoxide compounds, dialkylaluminum hydride compounds, and combinations thereof. Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof.

The present invention contemplates a method of precontacting a hybrid metallocene compound with an organoaluminum compound and an olefin monomer to form a precontacted mixture, prior to contacting this precontacted mixture with an activator-support to form a catalyst composition. When the catalyst composition is prepared in this manner, typically, though not necessarily, a portion of the organoaluminum compound can be added to the precontacted mixture and another portion of the organoaluminum compound can be added to the postcontacted mixture prepared when the precontacted mixture is contacted with the solid oxide activator-support. However, the entire organoaluminum compound can be used to prepare the catalyst composition in either the precontacting or postcontacting step. Alternatively, all the catalyst components can be contacted in a single step.

Further, more than one organoaluminum compound can be used in either the precontacting or the postcontacting step. When an organoaluminum compound is added in multiple steps, the amounts of organoaluminum compound disclosed herein include the total amount of organoaluminum compound used in both the precontacted and postcontacted mixtures, and any additional organoaluminum compound added to the polymerization reactor. Therefore, total amounts of organoaluminum compounds are disclosed regardless of whether a single organoaluminum compound or more than one organoaluminum compound is used.

Aluminoxane Compounds

The present invention further provides a catalyst composition which can comprise an aluminoxane compound. As used herein, the term "aluminoxane" refers to aluminoxane compounds, compositions, mixtures, or discrete species, regardless of how such aluminoxanes are prepared, formed or otherwise provided. For example, a catalyst composition comprising an aluminoxane compound can be prepared in which aluminoxane is provided as the poly(hydrocarbyl aluminum oxide), or in which aluminoxane is provided as the combination of an aluminum alkyl compound and a source of active protons such as water. Aluminoxanes also can be referred to as poly(hydrocarbyl aluminum oxides) or organoaluminoxanes.

The other catalyst components typically can be contacted with the aluminoxane in a saturated hydrocarbon compound solvent, though any solvent that is substantially inert to the reactants, intermediates, and products of the activation step can be used. The catalyst composition formed in this manner can be collected by any suitable method, for example, by filtration. Alternatively, the catalyst composition can be introduced into the polymerization reactor without being isolated.

The aluminoxane compound of this invention can be an oligomeric aluminum compound comprising linear structures, cyclic structures, or cage structures, or mixtures of all three. Cyclic aluminoxane compounds having the formula:

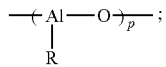

wherein R in this formula can be a linear or branched alkyl having from 1 to 10 carbon atoms, and p in this formula can be an integer from 3 to 20, are encompassed by this invention. The AlRO moiety shown here also can constitute the repeating unit in a linear aluminoxane. Thus, linear aluminoxanes having the formula:

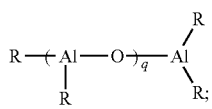

wherein R in this formula can be a linear or branched alkyl having from 1 to 10 carbon atoms, and q in this formula can be an integer from 1 to 50, are also encompassed by this invention.

Further, aluminoxanes can have cage structures of the formula $R^t_{5r+\alpha}R^b_{r-\alpha}Al_{4r}O_{3r}$, wherein $R^t$ can be a terminal linear or branched alkyl group having from 1 to 10 carbon atoms; $R^b$ can be a bridging linear or branched alkyl group having from 1 to 10 carbon atoms; r can be 3 or 4; and α can be equal to $n_{Al(3)} - n_{O(2)} + n_{O(4)}$, wherein $n_{Al(3)}$ is the number of three coordinate aluminum atoms, $n_{O(2)}$ is the number of two coordinate oxygen atoms, and $n_{O(4)}$ is the number of 4 coordinate oxygen atoms.

Thus, aluminoxanes which can be employed in the catalyst compositions of the present invention can be represented generally by formulas such as $(R-Al-O)_p$, $R(R-Al-O)_q AlR_2$, and the like. In these formulas, the R group typically can be a linear or branched $C_1$-$C_6$ alkyl, such as methyl, ethyl, propyl, butyl, pentyl, or hexyl. Examples of aluminoxane compounds that can be used in accordance with the present invention can include, but are not limited to, methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, iso-pentylaluminoxane, neopentylaluminoxane, and the like, or any combination thereof. Methylaluminoxane, ethylaluminoxane, and iso-butylaluminoxane can be prepared from trimethylaluminum, triethylaluminum, or triisobutylaluminum, respectively, and sometimes are referred to as poly(methyl aluminum oxide), poly(ethyl aluminum oxide), and poly (isobutyl aluminum oxide), respectively. It is also within the scope of the invention to use an aluminoxane in combination with a trialkylaluminum, such as that disclosed in U.S. Pat. No. 4,794,096, incorporated herein by reference in its entirety.

The present invention contemplates many values of p and q in the aluminoxane formulas $(R-Al-O)_p$ and $R(R-Al-O)_q AlR_2$, respectively. In some aspects, p and q can be at least 3. However, depending upon how the organoaluminoxane is prepared, stored, and used, the value of p and q can vary within a single sample of aluminoxane, and such combinations of organoaluminoxanes are contemplated herein.

In preparing a catalyst composition containing an aluminoxane, the molar ratio of the total moles of aluminum in the aluminoxane (or aluminoxanes) to the total moles of metallocene compound(s) in the composition generally can be between about 1:10 and about 100,000:1. In another aspect, the molar ratio can be in a range from about 5:1 to about 15,000:1. Optionally, aluminoxane can be added to a polymerization zone in ranges from about 0.01 mg/L to about 1000 mg/L, from about 0.1 mg/L to about 100 mg/L, or from about 1 mg/L to about 50 mg/L.

Organoaluminoxanes can be prepared by various procedures. Examples of organoaluminoxane preparations are disclosed in U.S. Pat. Nos. 3,242,099 and 4,808,561, the disclosures of which are incorporated herein by reference in their entirety. For example, water in an inert organic solvent can be reacted with an aluminum alkyl compound, such as $(R^1)_3Al$, to form the desired organoaluminoxane compound. While not intending to be bound by this statement, it is believed that this synthetic method can afford a mixture of both linear and cyclic R—Al—O aluminoxane species, both of which are encompassed by this invention. Alternatively, organoaluminoxanes can be prepared by reacting an aluminum alkyl compound, such as $(R^1)_3Al$, with a hydrated salt, such as hydrated copper sulfate, in an inert organic solvent.

Organoboron/Organoborate Compounds

According to another aspect of the present invention, the catalyst composition can comprise an organoboron or organoborate compound. Such compounds can include neutral boron compounds, borate salts, and the like, or combinations thereof. For example, fluoroorgano boron compounds and fluoroorgano borate compounds are contemplated.

Any fluoroorgano boron or fluoroorgano borate compound can be utilized with the present invention. Examples of fluoroorgano borate compounds that can be used in the present invention can include, but are not limited to, fluorinated aryl borates such as N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, or mixtures thereof. Examples of fluoroorgano boron compounds that can be used as co-catalysts or activators in the present invention can include, but are not limited to, tris(pentafluorophenyl)boron, tris[3,5-bis(trifluoromethyl)phenyl]boron, and the like, or mixtures thereof. Although not intending to be bound by the following theory, these examples of fluoroorgano borate and fluoroorgano boron compounds, and related compounds, are thought to form "weakly-coordinating" anions when combined with hybrid metallocene compounds, as disclosed in U.S. Pat. No. 5,919,983, the disclosure of which is incorporated herein by reference in its entirety. Applicants also contemplate the use of diboron, or bis-boron, compounds or other bifunctional compounds containing two or more boron atoms in the chemical structure, such as disclosed in J. Am. Chem. Soc., 2005, 127, pp. 14756-14768, the content of which is incorporated herein by reference in its entirety.

Generally, any amount of organoboron compound can be used. According to one aspect of this invention, the molar ratio of the total moles of organoboron or organoborate compound (or compounds) to the total moles of hybrid metallocene compound (or compounds) in the catalyst composition can be in a range from about 0.1:1 to about 15:1. Typically, the amount of the fluoroorgano boron or fluoroorgano borate compound used can be from about 0.5 moles to about 10 moles of boron/borate compound per mole of hybrid metallocene compound(s). According to another aspect of this invention, the amount of fluoroorgano boron or fluoroorgano borate compound can be from about 0.8 moles to about 5 moles of boron/borate compound per mole of hybrid metallocene compound(s).

Ionizing Ionic Compounds

The present invention further provides a catalyst composition which can comprise an ionizing ionic compound. An ionizing ionic compound is an ionic compound that can function as an activator or co-catalyst to enhance the activity of the catalyst composition. While not intending to be bound by theory, it is believed that the ionizing ionic compound is capable of reacting with a hybrid metallocene compound and converting the metallocene into one or more cationic metallocene compounds, or incipient cationic metallocene compounds. Again, while not intending to be bound by theory, it is believed that the ionizing ionic compound can function as an ionizing compound by completely or partially extracting an anionic ligand, possibly a non-alkadienyl ligand such as $X^1$ or $X^2$, from the hybrid metallocene. However, the ionizing ionic compound can be an activator or co-catalyst regardless of whether it is ionizes the hybrid metallocene, abstracts a $X^1$ or $X^2$ ligand in a fashion as to form an ion pair, weakens the metal-$X^1$ or metal-$X^2$ bond in the hybrid metallocene, simply coordinates to a $X^1$ or $X^2$ ligand, or activates the hybrid metallocene compound by some other mechanism.

Further, it is not necessary that the ionizing ionic compound activate the hybrid metallocene compound only. The activation function of the ionizing ionic compound can be evident in the enhanced activity of catalyst composition as a whole, as compared to a catalyst composition that does not contain an ionizing ionic compound.

Examples of ionizing ionic compounds can include, but are not limited to, the following compounds: tri(n-butyl)ammonium tetrakis(p-tolyl)borate, tri(n-butyl)ammonium tetrakis (m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoro-methyl)phenyl]borate, triphenylcarbenium tetrakis (pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl) aluminate, potassium tetrakis(2,4-dimethylphenyl)aluminate, potassium tetrakis(3,5-dimethylphenyl)aluminate, potassium tetrafluoroaluminate, and the like, or combinations thereof. Ionizing ionic compounds useful in this invention are not limited to these; other examples of ionizing ionic compounds are disclosed in U.S. Pat. Nos. 5,576,259 and 5,807,938, the disclosures of which are incorporated herein by reference in their entirety.

Olefin Monomers

Unsaturated reactants that can be employed with catalyst compositions and polymerization processes of this invention typically can include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally can contain a major amount of ethylene (>50 mole percent) and a minor amount of comonomer (<50 mole percent), though this is not a requirement. Comonomers that can be copolymerized with ethylene often can have from 3 to 20 carbon atoms in their molecular chain.

Acyclic, cyclic, polycyclic, terminal ($\alpha$), internal, linear, branched, substituted, unsubstituted, functionalized, and non-functionalized olefins can be employed in this invention. For example, typical unsaturated compounds that can be polymerized with the catalyst compositions of this invention can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described above. Styrene can also be employed as a monomer in the present invention. In an aspect, the olefin monomer can be a $C_2$-$C_{10}$ olefin; alternatively, the olefin monomer can be ethylene; or alternatively, the olefin monomer can be propylene.

When a copolymer (or alternatively, a terpolymer) is desired, the olefin monomer can comprise, for example, ethylene or propylene, which is copolymerized with at least one comonomer. According to one aspect of this invention, the olefin monomer in the polymerization process can comprise ethylene. In this aspect, examples of suitable olefin comonomers an include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to one aspect of the present invention, the comonomer can comprise 1-butene, 1-pentene, 1-hexene, 1-octene, 1-decene, styrene, or any combination thereof.

Generally, the amount of comonomer introduced into a reactor zone to produce a copolymer can be from about 0.01 to about 50 weight percent of the comonomer based on the total weight of the monomer and comonomer. According to another aspect of the present invention, the amount of comonomer introduced into a reactor zone can be from about 0.01 to about 40 weight percent comonomer based on the total weight of the monomer and comonomer. In still another aspect, the amount of comonomer introduced into a reactor zone can be from about 0.1 to about 35 weight percent comonomer based on the total weight of the monomer and comonomer. Yet, in another aspect, the amount of comonomer introduced into a reactor zone can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might. According to one aspect of the present invention, at least one monomer/reactant can be ethylene, so the polymerizations are either a homopolymerization involving only ethylene, or copolymerizations with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Catalyst Compositions

In some aspects, the present invention employs catalyst compositions containing a hybrid metallocene having a heteroatom-containing ligand and an activator, while in other aspects, the present invention employs catalyst compositions containing a hybrid metallocene having a heteroatom-containing ligand and an activator-support. These catalyst compositions can be utilized to produce polyolefins—homopolymers, copolymers, and the like—for a variety of end-use applications.

Hybrid metallocene compounds having formulas (I), (II), (III), and (IV) were discussed above. In aspects of the present invention, it is contemplated that the catalyst composition can contain more than one hybrid metallocene compound. Further, additional metallocene compounds—other than those having formulas (I), (II), (III), and/or (IV)—can be employed in the catalyst composition and/or the polymerization process, provided that the additional metallocene compound(s) does not detract from the advantages disclosed herein. Additionally, more than one activator and/or more than one activator-support also may be utilized.

Generally, catalyst compositions of the present invention can comprise a hybrid metallocene compound having formula (I), (II), (III), and/or (IV) and an activator. In aspects of the invention, the activator can comprise an activator-support. Activator-supports useful in the present invention were disclosed above. Such catalyst compositions can further comprise one or more than one organoaluminum compound or compounds (suitable organoaluminum compounds also were discussed above). Thus, a catalyst composition of this invention can comprise a hybrid metallocene compound having formula (I), (II), (III), and/or (IV), an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Accordingly, a catalyst composition consistent with this invention can comprise (or consist essentially of, or consist of) a hybrid metallocene compound having formula (I), (II), (III), and/or (IV), sulfated alumina (or fluorided silica-alumina), and triethylaluminum (or triisobutylaluminum).

In another aspect of the present invention, a catalyst composition is provided which comprises a hybrid metallocene compound having formula (I), (II), (III), and/or (IV), an activator-support, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, to be discussed below, in the absence of these additional materials. For example, a catalyst composition of the present invention can consist essentially of a metallocene compound having formula (I), (II), (III), and/or (IV), an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising a hybrid metallocene compound having formula (I), (II), (III), and/or (IV), and an activator-support can further comprise an optional co-catalyst. Suitable co-catalysts in this aspect include, but are not limited to, aluminoxane compounds, organoboron or organoborate compounds, ionizing ionic compounds, and the like, or any combination thereof. More than one co-catalyst can be present in the catalyst composition.

In a different aspect, a catalyst composition is provided which does not require an activator-support. Such a catalyst composition can comprise a hybrid metallocene compound having formula (I), (II), (III), and/or (IV), and an activator, wherein the activator comprises an aluminoxane compound, an organoboron or organoborate compound, an ionizing ionic compound, or combinations thereof.

This invention further encompasses methods of making these catalyst compositions, such as, for example, contacting the respective catalyst components in any order or sequence.

The hybrid metallocene compound having formula (I), (II), (III), and/or (IV) can be precontacted with an olefinic monomer if desired, not necessarily the olefin monomer to be polymerized, and an organoaluminum compound for a first period of time prior to contacting this precontacted mixture with an activator-support. The first period of time for contact, the precontact time, between the metallocene compound, the olefinic monomer, and the organoaluminum compound typically ranges from a time period of about 1 minute to about 24 hours, for example, from about 3 minutes to about 1 hour. Precontact times from about 10 minutes to about 30 minutes are also employed. Alternatively, the precontacting process is carried out in multiple steps, rather than a single step, in which multiple mixtures are prepared, each comprising a different set of catalyst components. For example, at least two catalyst components are contacted forming a first mixture, followed by contacting the first mixture with at least one other catalyst component forming a second mixture, and so forth.

Multiple precontacting steps can be carried out in a single vessel or in multiple vessels. Further, multiple precontacting steps can be carried out in series (sequentially), in parallel, or a combination thereof. For example, a first mixture of two catalyst components can be formed in a first vessel, a second mixture comprising the first mixture plus one additional catalyst component can be formed in the first vessel or in a second vessel, which is typically placed downstream of the first vessel.

In another aspect, one or more of the catalyst components can be split and used in different precontacting treatments. For example, part of a catalyst component is fed into a first precontacting vessel for precontacting with at least one other catalyst component, while the remainder of that same catalyst component is fed into a second precontacting vessel for precontacting with at least one other catalyst component, or is fed directly into the reactor, or a combination thereof. The precontacting can be carried out in any suitable equipment, such as tanks, stirred mix tanks, various static mixing devices, a flask, a vessel of any type, or combinations of these apparatus.

In another aspect of this invention, the various catalyst components (for example, a hybrid metallocene compound having formula (I), (II), (III), and/or (IV), activator-support, organoaluminum co-catalyst, and optionally an unsaturated hydrocarbon) can be contacted in the polymerization reactor simultaneously while the polymerization reaction is proceeding. Alternatively, any two or more of these catalyst components can be precontacted in a vessel prior to entering the reaction zone. This precontacting step can be continuous, in which the precontacted product is fed continuously to the reactor, or it can be a stepwise or batchwise process in which a batch of precontacted product is added to make a catalyst composition. This precontacting step can be carried out over a time period that can range from a few seconds to as much as several days, or longer. In this aspect, the continuous precontacting step generally lasts from about 1 second to about 1 hour. In another aspect, the continuous precontacting step lasts from about 10 seconds to about 45 minutes, or from about 1 minute to about 30 minutes.

Once the precontacted mixture of the metallocene compound having formula (I), (II), (III), and/or (IV), the olefin monomer, and the organoaluminum co-catalyst is contacted with the activator-support, this composition (with the addition of the activator-support) is termed the "postcontacted mixture." The postcontacted mixture optionally can remain in contact for a second period of time, the postcontact time, prior to initiating the polymerization process. Postcontact times between the precontacted mixture and the activator-support generally range from about 1 minute to about 24 hours. In a further aspect, the postcontact time is in a range from about 3 minutes to about 1 hour. The precontacting step, the postcontacting step, or both, can increase the productivity of the polymer as compared to the same catalyst composition that is prepared without precontacting or postcontacting. However, neither a precontacting step nor a postcontacting step is required.

The postcontacted mixture can be heated at a temperature and for a time period sufficient to allow adsorption, impregnation, or interaction of precontacted mixture and the activator-support, such that a portion of the components of the precontacted mixture is immobilized, adsorbed, or deposited thereon. Where heating is employed, the postcontacted mixture generally is heated to a temperature of from between about −15° C. to about 70° C., or from about 0° C. to about 40° C.

When a precontacting step is used, the molar ratio of the total moles of olefin monomer to total moles of metallocene(s) in the precontacted mixture typically can be in a range from about 1:10 to about 100,000:1. Total moles of each component are used in this ratio to account for aspects of this invention where more than one olefin monomer and/or more than one metallocene compound is employed in a precontacting step. Further, this molar ratio can be in a range from about 10:1 to about 1,000:1 in another aspect of the invention.

Generally, the weight ratio of organoaluminum compound to activator-support can be in a range from about 10:1 to about 1:1000. If more than one organoaluminum compound and/or more than one activator-support is employed, this ratio is based on the total weight of each respective component. In another aspect, the weight ratio of the organoaluminum compound to the activator-support can be in a range from about 3:1 to about 1:100, or from about 1:1 to about 1:50.

In some aspects of this invention, the weight ratio of metallocene compound(s) to activator-support can be in a range from about 1:1 to about 1:1,000,000. If more than one activator-support is employed, this ratio is based on the total weight of the activator-support. In another aspect, this weight ratio can be in a range from about 1:5 to about 1:100,000, or from about 1:10 to about 1:10,000. Yet, in another aspect, the weight ratio of the metallocene compound(s) to the activator-support can be in a range from about 1:20 to about 1:1000.

Catalyst compositions of the present invention generally have a catalyst activity greater than about 100 grams of polyethylene (homopolymer, copolymer, etc., as the context requires) per gram of activator-support per hour (abbreviated g/g/hr). In another aspect, the catalyst activity can be greater than about 150, greater than about 250, or greater than about 500 g/g/hr. In still another aspect, catalyst compositions of this invention can be characterized by having a catalyst activity greater than about 550, greater than about 650, or greater than about 750 g/g/hr. Yet, in another aspect, the catalyst activity can be greater than about 1000 g/g/hr. This activity is measured under slurry polymerization conditions using isobutane as the diluent, at a polymerization temperature of about 90° C. and a reactor pressure of about 400 psig (2.75 MPa).

In accordance with another aspect of the present invention, catalyst compositions disclosed herein can have a catalyst activity greater than about 500 kilograms of polyethylene (homopolymer, copolymer, etc., as the context requires) per mol of metallocene per hour (abbreviated kg/mol/hr). In another aspect, the catalyst activity of the catalyst composition can be greater than about 1000, greater than about 2000, or greater than about 3000 kg/mol/hr. In still another aspect, catalyst compositions of this invention can be characterized by having a catalyst activity greater than about 5000, greater than about 8000, or greater than about 10,000 kg/mol/hr. Yet, in another aspect, the catalyst activity can be greater than about 15,000 kg/mol/hr. This activity is measured under slurry polymerization conditions using isobutane as the diluent, at a polymerization temperature of about 90° C. and a reactor pressure of about 400 psig (2.75 MPa).

As discussed above, any combination of the metallocene compound having formula (I), (II), (III), and/or (IV), the activator-support, the organoaluminum compound, and the olefin monomer, can be precontacted in some aspects of this invention. When any precontacting occurs with an olefinic monomer, it is not necessary that the olefin monomer used in the precontacting step be the same as the olefin to be polymerized. Further, when a precontacting step among any combination of the catalyst components is employed for a first period of time, this precontacted mixture can be used in a subsequent postcontacting step between any other combination of catalyst components for a second period of time. For example, the metallocene compound, the organoaluminum compound, and 1-hexene can be used in a precontacting step for a first period of time, and this precontacted mixture then can be contacted with the activator-support to form a postcontacted mixture that is contacted for a second period of time prior to initiating the polymerization reaction. For example, the first period of time for contact, the precontact time, between any combination of the metallocene compound, the olefinic monomer, the activator-support, and the organoaluminum compound can be from about 1 minute to about 24 hours, from about 3 minutes to about 1 hour, or from about 10 minutes to about 30 minutes. The postcontacted mixture optionally is allowed to remain in contact for a second period of time, the postcontact time, prior to initiating the polymerization process. According to one aspect of this invention, postcontact times between the precontacted mixture and any remaining catalyst components is from about 1 minute to about 24 hours, or from about 5 minutes to about 1 hour.

Polymerization Process

Catalyst compositions of the present invention can be used to polymerize olefins to form homopolymers, copolymers, terpolymers, and the like. One such process for polymerizing olefins in the presence of a catalyst composition of the present invention can comprise contacting the catalyst composition with an olefin monomer and optionally an olefin comonomer (one or more) under polymerization conditions to produce an olefin polymer, wherein the catalyst composition can comprise a metallocene compound having formula (I), (II), (III), and/or (IV), and an activator. Metallocene compounds having formula (I), (II), (III), and/or (IV), were discussed above.

In accordance with one aspect of the invention, the polymerization process can employ a catalyst composition comprising a hybrid metallocene compound having formula (I), (II), (III), and/or (IV), and an activator, wherein the activator comprises an activator-support. Activator-supports useful in the polymerization processes of the present invention were disclosed above. The catalyst composition can further comprise one or more than one organoaluminum compound or compounds (suitable organoaluminum compounds also were discussed above). Thus, a process for polymerizing olefins in the presence of a catalyst composition can employ a catalyst composition comprising a hybrid metallocene compound having formula (I), (II), (III), and/or (IV), an activator-support, and an organoaluminum compound. In some aspects, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In some aspects, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof.

In accordance with another aspect of the invention, the polymerization process can employ a catalyst composition comprising a hybrid metallocene compound having formula (I), (II), (III), and/or (IV), and an activator, wherein the activator comprises an aluminoxane compound, an organoboron or organoborate compound, an ionizing ionic compound, or combinations thereof.

The catalyst compositions of the present invention are intended for any olefin polymerization method using various types of polymerization reactors. As used herein, "polymerization reactor" includes any polymerization reactor capable of polymerizing olefin monomers and comonomers (one or more than one comonomer) to produce homopolymers, copolymers, terpolymers, and the like. The various types of reactors include those that may be referred to as a batch reactor, slurry reactor, gas-phase reactor, solution reactor, high pressure reactor, tubular reactor, autoclave reactor, and the like, or combinations thereof. The polymerization conditions for the various reactor types are well known to those of skill in the art. Gas phase reactors may comprise fluidized bed reactors or staged horizontal reactors. Slurry reactors may comprise vertical or horizontal loops. High pressure reactors may comprise autoclave or tubular reactors. Reactor types can include batch or continuous processes. Continuous processes could use intermittent or continuous product discharge. Processes may also include partial or full direct recycle of unreacted monomer, unreacted comonomer, and/or diluent.

Polymerization reactor systems of the present invention may comprise one type of reactor in a system or multiple reactors of the same or different type. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas phase reactors, a combination of loop and gas phase reactors, multiple high pressure reactors, or a combination of high pressure with loop and/or gas phase reactors. The multiple reactors may be operated in series, in parallel, or both.

According to one aspect of the invention, the polymerization reactor system may comprise at least one loop slurry reactor comprising vertical or horizontal loops. Monomer, diluent, catalyst, and comonomer may be continuously fed to a loop reactor where polymerization occurs. Generally, continuous processes may comprise the continuous introduction of monomer/comonomer, a catalyst, and a diluent into a polymerization reactor and the continuous removal from this reactor of a suspension comprising polymer particles and the diluent. Reactor effluent may be flashed to remove the solid polymer from the liquids that comprise the diluent, monomer and/or comonomer. Various technologies may be used for this separation step including but not limited to, flashing that may include any combination of heat addition and pressure reduction; separation by cyclonic action in either a cyclone or hydrocyclone; or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, and 6,833,415, each of which is incorporated herein by reference in its entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect of this invention, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, and 5,436,304, each of which is incorporated by reference in its entirety herein.

According to still another aspect of the invention, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect of the invention, the polymerization reactor may comprise a solution polymerization reactor wherein the monomer/comonomer are contacted with the catalyst composition by suitable stirring or other means. A carrier comprising an inert organic diluent or excess monomer may be employed. If desired, the monomer/comonomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present invention may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature may be any temperature below the de-polymerization temperature according to the Gibbs Free energy equation. Typically, this includes from about 60° C. to about 280° C., for example, or from about 60° C. to about 110° C., depending upon the type of polymerization reactor. In some reactor systems, the polymerization temperature generally is within a range from about 70° C. to about 90° C., or from about 75° C. to about 85° C.

Suitable pressures will also vary according to the reactor and polymerization type. The pressure for liquid phase polymerizations in a loop reactor is typically less than 1000 psig (6.9 MPa). Pressure for gas phase polymerization is usually at about 200 to 500 psig (1.4 to 3.4 MPa). High pressure polymerization in tubular or autoclave reactors is generally run at about 20,000 to 75,000 psig (138 to 517 MPa). Polymerization reactors can also be operated in a supercritical region occurring at generally higher temperatures and pressures. Operation above the critical point of a pressure/temperature diagram (supercritical phase) may offer advantages.

Aspects of this invention are directed to olefin polymerization processes comprising contacting a catalyst composition with an olefin monomer and optionally an olefin comonomer under polymerization conditions to produce an olefin polymer. The olefin polymer produced by the process can have less than about 0.002 long chain branches per 1000 total carbon atoms, and/or a ratio of Mw/Mn in a range from about 3 to about 20, and/or a ratio of vinyl end groups to saturated end groups in a range from about 0.4 to about 0.9. In addition, or alternatively, the olefin polymer can have a melt index less than 2.5, and/or a Mn in a range from about 15,000 to about 50,000, and/or a Mw in a range from about 100,000 to about 300,000, and/or a Mz in a range from about 750,000 to about 3,500,000, and/or a Mw/Mn in a range from about 5 to about 15, and/or less than about 0.001 long chain branches per 1000 total carbon atoms.

Aspects of this invention also are directed to olefin polymerization processes conducted in the absence of added hydrogen. In this disclosure, "added hydrogen" will be denoted as the feed ratio of hydrogen to olefin monomer entering the reactor (in units of ppm). An olefin polymerization process of this invention can comprise contacting a catalyst composition with an olefin monomer and optionally an olefin comonomer under polymerization conditions to produce an olefin polymer, wherein the catalyst composition comprises a hybrid metallocene compound and an activator, wherein the polymerization process is conducted in the absence of added hydrogen. As disclosed above, the hybrid metallocene can have formula (I), formula (II), formula (III), and/or formula (IV). As one of ordinary skill in the art would recognize, hydrogen can be generated in-situ by metallocene catalyst compositions in various olefin polymerization processes, and the amount generated may vary depending upon the specific catalyst composition and metallocene compound(s) employed, the type of polymerization process used, the polymerization reaction conditions utilized, and so forth.

In other aspects, it may be desirable to conduct the polymerization process in the presence of a certain amount of added hydrogen. Accordingly, an olefin polymerization process of this invention can comprise contacting a catalyst composition with an olefin monomer and optionally an olefin comonomer under polymerization conditions to produce an olefin polymer, wherein the catalyst composition comprises a hybrid metallocene compound and an activator, wherein the polymerization process is conducted in the presence of added hydrogen. For example, the ratio of hydrogen to the olefin monomer in the polymerization process can be controlled, often by the feed ratio of hydrogen to the olefin monomer entering the reactor. The added hydrogen to olefin monomer ratio in the process can be controlled at a weight ratio which falls within a range from about 25 ppm to about 1500 ppm, from about 50 to about 1000 ppm, or from about 100 ppm to about 750 ppm.

In some aspects of this invention, the feed or reactant ratio of hydrogen to olefin monomer can be maintained substantially constant during the polymerization run for a particular polymer grade. That is, the hydrogen:olefin monomer ratio can be selected at a particular ratio within a range from about 5 ppm up to about 1000 ppm or so, and maintained at the ratio to within about +/−25% during the polymerization run. For instance, if the target ratio is 100 ppm, then maintaining the hydrogen:olefin monomer ratio substantially constant would entail maintaining the feed ratio between about 75 ppm and about 125 ppm. Further, the addition of comonomer (or comonomers) can be, and generally is, substantially constant throughout the polymerization run for a particular polymer grade.

However, in other aspects, it is contemplated that monomer, comonomer (or comonomers), and/or hydrogen can be periodically pulsed to the reactor, for instance, in a manner similar to that employed in U.S. Pat. No. 5,739,220 and U.S. Patent Publication No. 2004/0059070, the disclosures of which are incorporated herein by reference in their entirety.

The concentration of the reactants entering the polymerization reactor can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers produced by any of the polymerization processes disclosed herein. Articles of manufacture can be formed from, and/or can comprise, the polymers produced in accordance with this invention.

Polymers and Articles

If the resultant polymer produced in accordance with the present invention is, for example, a polymer or copolymer of ethylene, its properties can be characterized by various analytical techniques known and used in the polyolefin industry. Articles of manufacture can be formed from, and/or can comprise, the ethylene polymers of this invention, whose typical properties are provided below.

Polymers of ethylene (copolymers, terpolymers, etc.) produced in accordance with this invention generally can have a melt index from 0 to about 100 g/10 min. Melt indices in the range from 0 to about 75 g/10 min, from 0 to about 50 g/10 min, or from 0 to about 30 g/10 min, are contemplated in some aspects of this invention. For example, a polymer of the present invention can have a melt index (MI) in a range from 0 to about 25, from 0 to about 10, from 0 to about 5, from 0 to about 2, or from 0 to about 1 g/10 min.

Ethylene polymers produced in accordance with this invention can have a ratio of HLMI/MI of greater than about 25, such as, for example, greater than about 30, greater than about 40, or greater than about 50. Contemplated ranges for HLMI/MI include, but are not limited to, from about 50 to about 5000, from about 50 to about 4000, from about 50 to about 3000, from about 75 to about 3000, or from about 75 to about 2750.

The density of ethylene-based polymers produced using one or more hybrid metallocene compounds of the present invention typically can fall within the range from about 0.88 to about 0.97 g/cc. In one aspect of this invention, the polymer density can be in a range from about 0.90 to about 0.97 g/cc. Yet, in another aspect, the density generally can be in a range from about 0.91 to about 0.96 g/cc.

Ethylene polymers, such as copolymers and terpolymers, within the scope of the present invention generally can have a polydispersity index—a ratio of the weight-average molecular weight (Mw) to the number-average molecular weight (Mn)—in a range from about 3 to about 20. In some aspects disclosed herein, the ratio of Mw/Mn can be in a range from about 3.5 to about 20, from about 4 to about 20, from about 4 to about 18, from about 5 to about 18, from about 5 to about 16, from about 5 to about 14, from about 6 to about 14, or from about 6 to about 13.

The ratio of Mz/Mw for the polymers of this invention often can be in a range from about 3 to about 20. Mz is the z-average molecular weight. In accordance with one aspect, the Mz/Mw of the ethylene polymers of this invention can be in a range from about 3.5 to about 20, from about 4 to about 20, from about 6 to about 20, from about 6 to about 18, or from about 6 to about 16.

Generally, olefin polymers of the present invention have low levels of long chain branching, with typically less than 0.01 long chain branches (LCB's) per 1000 total carbon atoms. In some aspects, the number of LCB's per 1000 total carbon atoms can be less than about 0.008, or less than about 0.005. Furthermore, olefin polymers of the present invention (e.g., ethylene polymers) can have less than about 0.004, less than about 0.003, less than about 0.002, or less than about 0.001 LCB's per 1000 total carbon atoms, in other aspects of this invention.

Ethylene polymers can have a ratio of vinyl end groups to saturated end groups that falls generally within a range from about 0.4 to about 0.9. In some aspects this ratio of vinyl to saturated end groups can be in a range from about 0.5 to about 0.9, from about 0.6 to about 0.9, or from about 0.65 to about 0.85.

Ethylene polymers disclosed herein can have less than about 0.002 long chain branches per 1000 total carbon atoms, and/or a ratio of Mw/Mn in a range from about 3 to about 20, and/or a ratio of vinyl end groups to saturated end groups in a range from about 0.4 (or about 0.6) to about 0.9, and/or a melt index less than 2.5, and/or a Mn in a range from about 15,000 to about 50,000, and/or a Mw in a range from about 100,000 to about 300,000, and/or a Mz in a range from about 750,000 to about 3,500,000. Further, certain polymers can have a Mw/Mn in a range from about 5 to about 15, and/or less than about 0.001 long chain branches per 1000 total carbon atoms.

Polymers of ethylene, whether homopolymers, copolymers, terpolymers, and so forth, can be formed into various articles of manufacture. Articles which can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Applicants also contemplate a method for forming or preparing an article of manufacture comprising a polymer produced by any of the polymerization processes disclosed herein. For instance, a method can comprise (i) contacting a catalyst composition with an olefin monomer and optionally an olefin comonomer (one or more) under polymerization conditions to produce an olefin polymer, wherein the catalyst composition can comprise a metallocene compound having formula (I), (II), (III), and/or (IV), and an activator (e.g., an activator-support); and (ii) forming an article of manufacture comprising the olefin polymer. The forming step can comprise blending, melt processing, extruding, molding, or thermoforming, and the like, including combinations thereof.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

FIG. 1 presents the structures and corresponding abbreviations for hybrid metallocene compounds discussed in the examples that follow. Synthesis of the hybrid metallocene compounds was performed under purified nitrogen atmosphere using standard Schlenk line or glovebox techniques. The solvent THF was distilled from potassium, while anhydrous diethyl ether, methylene chloride, pentane, and toluene (Fisher Scientific Company) were stored over activated alumina. All solvents were degassed and stored under nitrogen. MET-A ($\eta^5$-cyclopentadienyl titanium trichloride), MET-B ($\eta^5$-pentamethylcyclopentadienyl titanium trichloride), and all of the organic ligands were purchased from Aldrich Chemical Company. Products were analyzed by $^1$H NMR (300 MHz, $C_6D_6$, referenced against residual $C_6D_6$ peak at 7.15 ppm).

Three general synthesis procedures were employed. In general procedure 1, one equivalent of LiOR$^A$ was added in one portion to a toluene solution of CpTiCl$_3$ (or Cp*TiCl$_3$) in a glovebox at room temperature (about 22-25° C.). The reaction mixture was stirred at 50° C. overnight (about 12-16 hr). After the white solid (LiCl) was removed by centrifuge or by filtration, the solvent was removed under vacuum, resulting in a red or orange solid. The solid was recrystallized in a solvent mixture of heptane and toluene to produce crystals of the respective hybrid titanium compound. In general procedure 2, a slight excess of NEt$_3$ in THF (or diethyl ether) was added dropwise to a THF (or diethyl ether) solution of CpTiCl$_3$ (or Cp*TiCl$_3$) and one equivalent of HOR$^A$. The resulting suspension was stirred overnight at room temperature. After the white solid (NEt$_3$.HCl) was removed by centrifuge or by filtration, the solvent was removed under vacuum, resulting in a red or orange solid. The solid was recrystallized in a solvent mixture of heptane and toluene to produce crystals of the respective hybrid titanium compound. In general procedure 3, one equivalent of HOR$^A$ in toluene was added to a toluene solution of CpTiCl$_3$, in a glovebox at room temperature. The reaction mixture was stirred overnight at 90° C. The solvent was removed under vacuum, resulting in an orange solid. The solid was recrystallized in a solvent mixture of heptane and toluene to produce crystals of the respective hybrid titanium compounds. Analogous synthesis schemes to these three general synthesis procedures can be employed to produce hybrid zirconium or hybrid hafnium compounds (e.g., using CpZrCl$_3$ or CpHfCl$_3$).

MET-D, MET-E, and MET-F were produced in accordance with one of these general synthesis procedures. The synthesis procedures for MET-C, MET-H, MET-I, MET-J, and MET-K are described in more detail in the examples that follow. MET-G was prepared in a manner similar to that of MET-H, but triphenylsilanol was utilized instead of 1,1,3-triphenyl-2-propyn-1-ol.

Polymerization experiments generally were performed as follows. The polymerizations were conducted for one hour in a one-gallon (3.785-L) stainless-steel autoclave reactor containing two liters of isobutane as diluent, and hydrogen added from a 325-cc auxiliary vessel. Delta P of hydrogen refers to the pressure drop in that auxiliary vessel from an initial 600 psig (4.1 MPa) starting pressure. Hybrid metallocene solutions (1 mg/mL) were prepared by dissolving 20 mg of the respective metallocene in 20 mL of toluene. Under isobutane purge, a triisobutylaluminum (TIBA) solution (25% in heptanes) was charged to a cold reactor, followed by the hybrid metallocene solution and sulfated alumina in toluene. The reactor was closed, and 2 L of isobutane were added. The reactor was heated to within about 5 degrees of the target run temperature, and the ethylene feed was opened. Ethylene was fed on demand to maintain the target reactor pressure. The reactor was maintained at the desired run temperature throughout the run by an automated heating-cooling system. Hydrogen was then introduced into the reactor during the polymerization process. For copolymerization, 1-hexene was flushed in with the initial ethylene charge. At the end of one hour, the isobutane and ethylene were vented from the reactor, the reactor was opened, and the polymer product was collected and dried.

Melt index (MI, g/10 min) was determined in accordance with ASTM D1238 condition F at 190° C. with a 2,160 gram weight.

High load melt index (HLMI, g/10 min) was determined in accordance with ASTM D1238 condition E at 190° C. with a 21,600 gram weight.

Polymer density was determined in grams per cubic centimeter (g/cc) on a compression molded sample, cooled at about 15° C. per hour, and conditioned for about 40 hours at room temperature in accordance with ASTM D1505 and ASTM D1928, procedure C.

Molecular weights and molecular weight distributions were obtained using a PL 220 SEC high temperature chromatography unit (Polymer Laboratories) with trichlorobenzene (TCB) as the solvent, with a flow rate of 1 mL/minute at a temperature of 145° C. BHT (2,6-di-tert-butyl-4-methylphenol) at a concentration of 0.5 g/L was used as a stabilizer in the TCB. An injection volume of 200 μL was used with a nominal polymer concentration of 1.5 mg/mL. Dissolution of the sample in stabilized TCB was carried out by heating at 150° C. for 5 hours with occasional, gentle agitation. The columns used were three PLgel Mixed A LS columns (7.8× 300 mm) and were calibrated with a broad linear polyethylene standard (Phillips Marlex® BHB 5003) for which the molecular weight had been determined In the examples that follow, Mn is the number-average molecular weight; Mw is the weight-average molecular weight; and Mz is the z-average molecular weight.

SEC-MALS combines the methods of size exclusion chromatography (SEC) with multi-angle light scattering (MALS) detection. A DAWN EOS 18-angle light scattering photometer (Wyatt Technology, Santa Barbara, Calif.) was attached to a PL-210 SEC system (Polymer Labs, UK) or a Waters 150 CV Plus system (Milford, Mass.) through a hot transfer line, thermally controlled at the same temperature as the SEC columns and its differential refractive index (DRI) detector (145° C.). At a flow rate setting of 0.7 mL/min, the mobile phase, 1,2,4-trichlorobenzene (TCB), was eluted through three, 7.5 mm×300 mm, 20 μm Mixed A-LS columns (Polymer Labs). Polyethylene (PE) solutions with concentrations of ~1.2 mg/mL, depending on samples, were prepared at 150° C. for 4 h before being transferred to the SEC injection vials sitting in a carousel heated at 145° C. For polymers of higher molecular weight, longer heating times were necessary in order to obtain true homogeneous solutions. In addition to acquiring a concentration chromatogram, seventeen light-scattering chromatograms at different angles were also acquired for each injection using Wyatt's Astra® software. At each chromatographic slice, both the absolute molecular weight (M) and root mean square (RMS) radius, also known as radius of gyration (Rg) were obtained from a Debye plot's intercept and slope, respectively. Methods for this process are detailed in Wyatt, P. J., *Anal. Chim. Acta*, 272, 1 (1993), which is incorporated herein by reference in its entirety.

The Zimm-Stockmayer approach was used to determine the amount of LCB. Since SEC-MALS measures M and Rg at each slice of a chromatogram simultaneously, the branching indices, $g_M$, as a function of M could be determined at each slice directly by determining the ratio of the mean square Rg of branched molecules to that of linear ones, at the same M, as shown in following equation (subscripts br and lin represent branched and linear polymers, respectively).

$$g_M = \frac{\langle R_g \rangle_{br}^2}{\langle R_g \rangle_{lin}^2}.$$

At a given $g_M$, the weight-averaged number of LCB per molecule ($B_{3w}$) was computed using Zimm-Stockmayer's equation, shown in the equation below, where the branches were assumed to be trifunctional, or Y-shaped.

$$g_M = \frac{6}{B_{3w}} \left\{ \frac{1}{2} \left( \frac{2+B_{3w}}{B_{3w}} \right)^{\frac{1}{2}} \ln\left[ \frac{(2+B_{3w})^{\frac{1}{2}} + (B_{3w})^{\frac{1}{2}}}{(2+B_{3w})^{\frac{1}{2}} - (B_{3w})^{\frac{1}{2}}} \right] - 1 \right\}.$$

LCB frequency (LCB$_{Mi}$), the number of LCB per 1000 C, of the i$^{th}$ slice was then computed straightforwardly using the following equation (M$_i$ is the MW of the i$^{th}$ slice):

$$LCB_{Mi} = 1000*14*B_{3w}/M_i.$$

The LCB distribution (LCBD) across the molecular weight distribution (MWD) was thus established for a full polymer.

43

Example 1

Synthesis of η$^5$-cyclopentadienyl(2,6-di-tert-butyl-4-methylphenoxy)titanium dichloride, MET-C MET-C was prepared as follows. Approximately 50 mL of toluene (~35° C.) was added to a flask with a mixture of 0.97 grams (4.42 mmol) of η$^5$-cyclopentadienyl titanium trichloride (MET-A) and 1 gram (4.42 mmol) of the lithium salt of 2,6-di-tert-butyl-4-methylphenol. The mixture was stirred at room temperature for 1-3 days. After solid LiCl was removed by centrifuge, and toluene was removed under vacuum, the resultant product was recrystallized in a solvent mixture of toluene and heptane. Approximately 1.39 g of MET-C were produced; the yield was 75%.

Example 2

Figure 2:
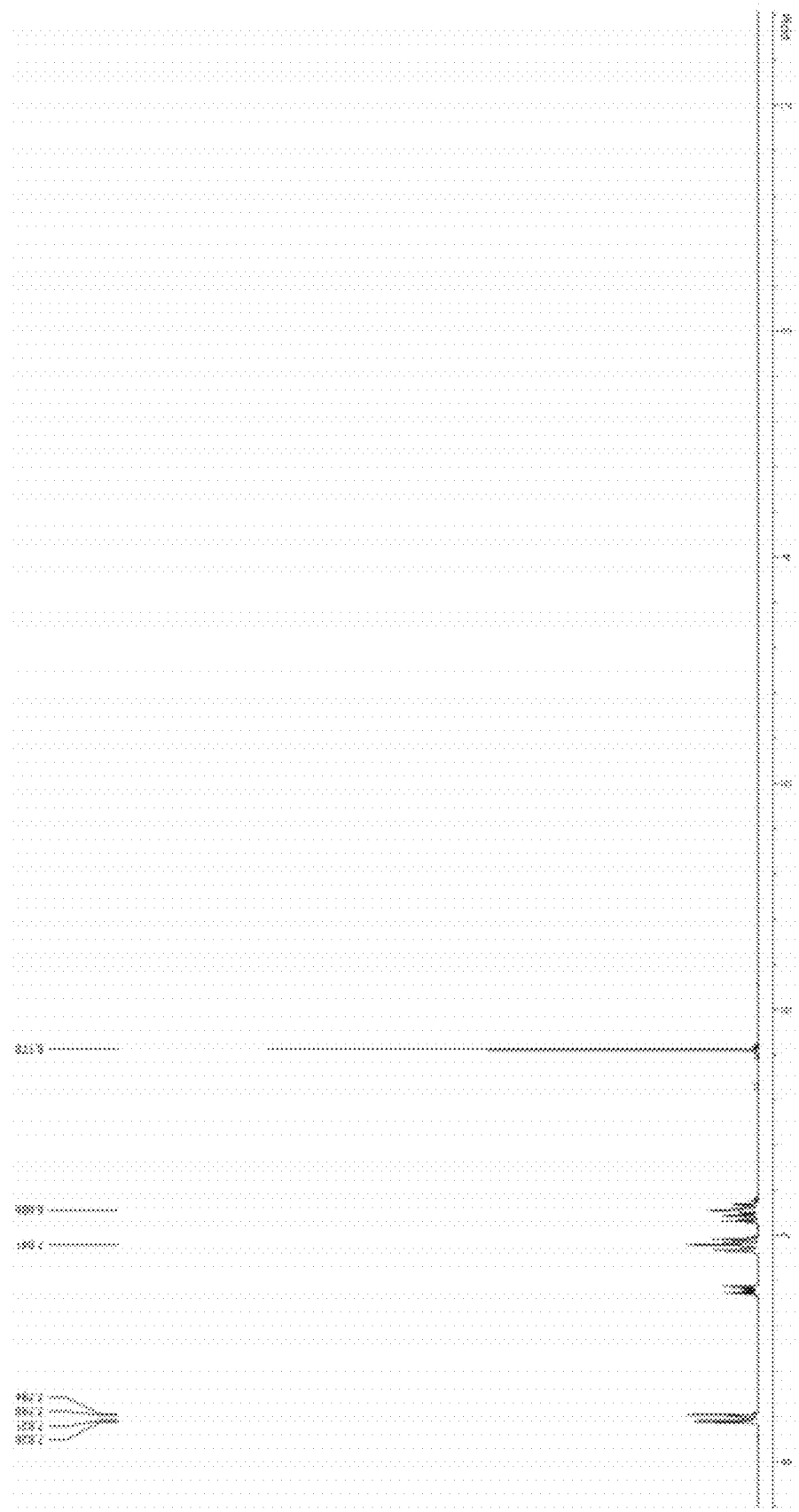
FIG. 2 presents a $^1$H-NMR plot of the MET-H product of Example 2.

Synthesis of η$^5$-cyclopentadienyl(1,1,3-triphenyl-2-propynoxy)titanium dichloride, MET-H MET-H was prepared as follows. Approximately 1.1 g (5 mmol) of if cyclopentadienyl titanium trichloride (MET-A) was dissolved in 30 mL of diethyl ether, and the solution was cooled from −30 to −70° C. A mixture of 1.42 grams (5 mmol) of 1,1,3-triphenyl-2-propyn-1-ol and 0.8 mL of dry Et$_3$N in 30 mL of diethyl ether was added over 30 min. The reaction mixture was stirred as room temperature overnight. A white solid was removed by centrifuge. A light orange solid was obtained after diethyl ether was removed under vacuum. The resultant product was recrystallized in toluene. Approximately 1.75 g of MET-H were produced; the yield was 80%. FIG. 2 illustrates the $^1$H-NMR analysis of the MET-H product.

Example 3

Synthesis of η$^5$-cyclopentadienyl(2,6-di-methoxyphenoxy)titanium dichloride, MET-I MET-I was prepared as follows. Approximately 0.5 grams (2.28 mmol) of η$^5$-cyclopentadienyl titanium trichloride (MET-A) and 0.35 grams (2.28 mmol) of 2,6-dimethoxyphenol were mixed in a cool toluene solvent (~0° C.). After the reaction mixture was stirred at room temperature for 30 minutes, the temperature was increased to 90° C. and stirred overnight. A dark red solid was obtained after toluene was removed under vacuum. The product was recrystallized in toluene. Approximately 0.67 g of MET-I were produced; the yield was 91%.

Example 4

Figure 3:
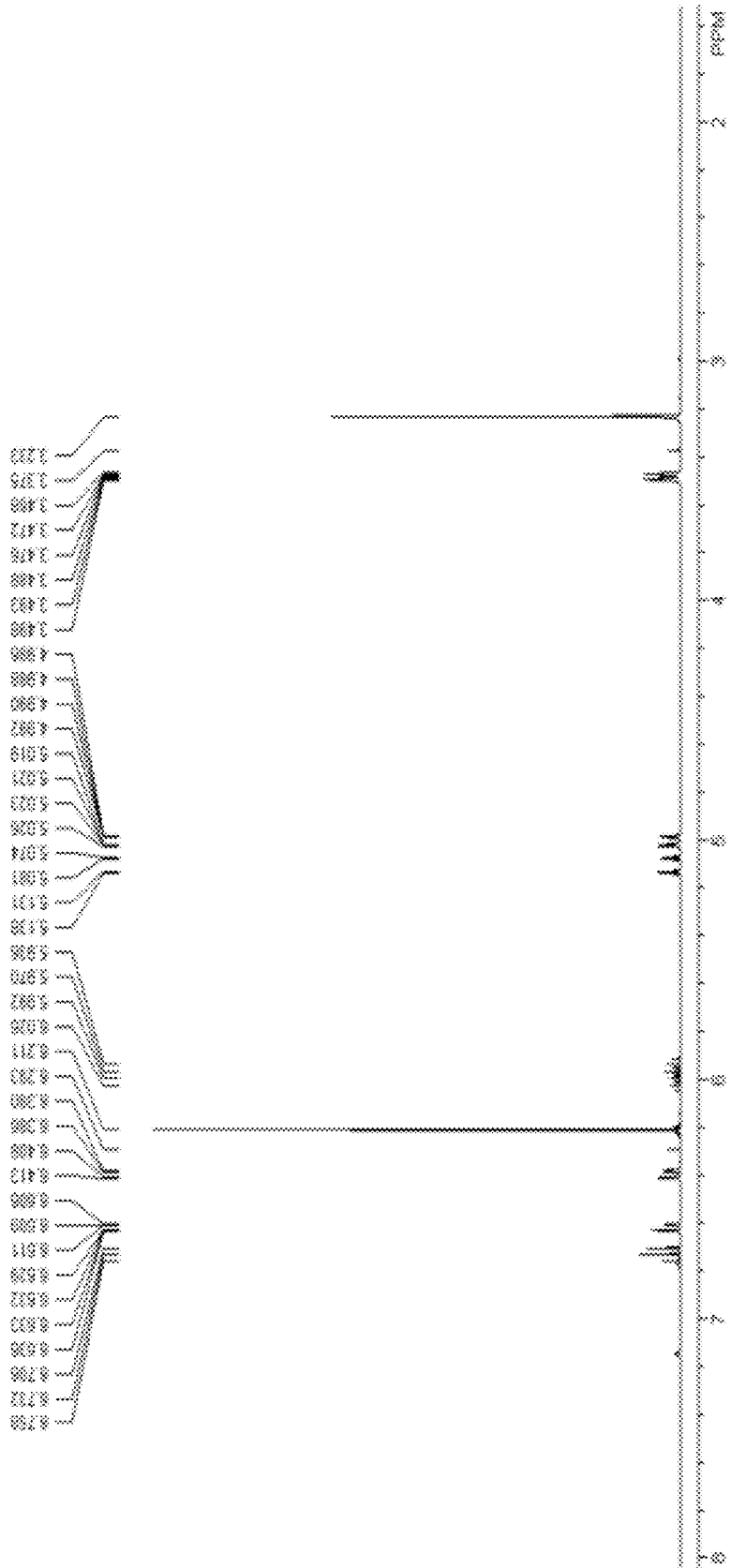
FIG. 3 presents a $^1$H-NMR plot of the MET-J product of Example 4.

Synthesis of η$^5$-cyclopentadienyl(6-allyl-2-methoxyphenoxy)titanium dichloride, MET-J MET-J was prepared as follows. A 1.5-g (9.1 mmol) 2-allyl-6-methoxyphenol solution in toluene was slowly added to a solution of 2 g (9.1 mmol) of η$^5$-cyclopentadienyl titanium trichloride (MET-A) in toluene at room temperature. After the reaction mixture was stirred at room temperature for 1 hr, the temperature was increased to 90° C. and stirred overnight. An orange solid was obtained after toluene was removed under vacuum. The product was recrystallized in toluene. Approximately 2.84 g of MET-J were produced; the yield was 90%. FIG. 3 illustrates the $^1$H-NMR analysis of the MET-J product.

Example 5

Figure 4:
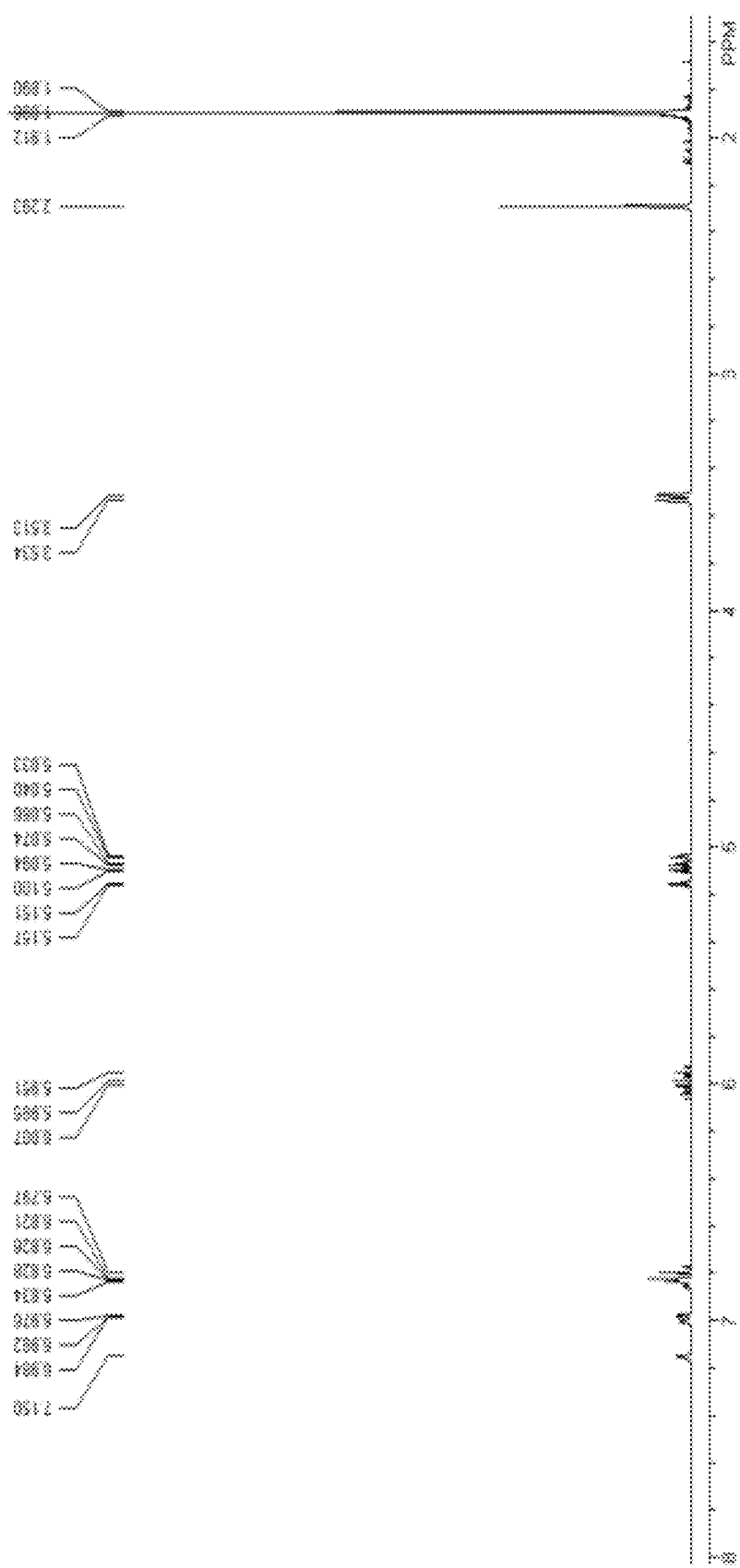
FIG. 4 presents a $^1$H-NMR plot of the MET-K product of Example 5.

Synthesis of η$^5$-pentamethylcyclopentadienyl(2-allyl-6-methylphenoxy)titanium dichloride, MET-K MET-K was prepared as follows. A 1-g (6.9 mmol) 2-allyl-6-methylphenol solution in toluene was slowly added to a solution of 2 g (6.9 mmol) of η$^5$-pentamethylcyclopentadienyl titanium trichloride (MET-B) in toluene at room temperature. After the reaction mixture was stirred at room temperature for 1 hr, the temperature was increased to 90° C. and stirred overnight. A red solid was obtained after toluene was removed under vacuum. The product was recrystallized in heptane. Approximately 2.2 g of MET-K were produced; the yield was 80%. FIG. 4 illustrates the $^1$H-NMR analysis of the MET-K product.

Example 6

Preparation of Sulfated Alumina Activator-Supports

Sulfated alumina activator-supports were prepared as follows. Bohemite was obtained from W.R. Grace Company under the designation "Alumina A" and having a surface area of about 300 m$^2$/g and a pore volume of about 1.3 mL/g This material was obtained as a powder having an average particle size of about 100 microns. This material was impregnated to incipient wetness with an aqueous solution of ammonium sulfate to equal about 15% sulfate. This mixture was then placed in a flat pan and allowed to dry under vacuum at approximately 110° C. for about 16 hours.

Alumina A, from W.R. Grace Company, was impregnated to incipient wetness with an aqueous solution of 0.08 g ammonium sulfate per mL of water. The alumina had a surface area of about 330 m$^2$/g and a pore volume of about 1.3 mL/gram. The amount of ammonium sulfate used was equal to 20% of the starting alumina, by weight. The resulting mixture was dried in a vacuum oven overnight at 120° C., and then screened through a 35 mesh screen. To calcine the resultant powdered mixture, the material was fluidized in a stream of dry air at 550° C. for 6 hours. Afterward, the sulfated alumina was collected and stored under dry nitrogen, and was used without exposure to the atmosphere. This sulfated alumina was used as the activator-support in Examples 7-61.

Examples 7-61

Polymerization Experiments Using Hybrid Metallocenes and Sulfated Alumina

Table 1 summarizes certain polymerization reaction conditions and polymer properties for Examples 7-61. Catalyst activities listed are in kilogram of polymer per mole of hybrid metallocene per hour (kg polymer/mol Ti/hr).

A representative polymerization with MET-D and sulfated alumina was conducted as follows. Approximately 2 mg of MET-D in 2 mL of toluene were mixed with 300 mg of sulfated alumina in 2 mL of toluene in a glass tube under nitrogen. After about one min, this slurry was added to the reactor at below 40° C. The reactor was sealed and 2 L of isobutane were added and the contents were stirred at 700 rpm. As the reactor temperature approached 85° C., ethylene addition was begun, and the set point of 90° C. was rapidly attained. The reactor was held at 90° C. for 60 min. The yield was 23,363 kg polymer/mol Ti/hr. See Example 10 in Table 1.

A representative polymerization with MET-E and sulfated alumina was conducted as follows. Approximately 2 mg of MET-E in 2 mL of toluene were mixed with 300 mg of sulfated alumina in 2 mL of toluene in a glass tube under nitrogen. After about one min, this slurry was added to the reactor at below 40° C. The reactor was sealed and 2 L of isobutane were added and the contents were stirred at 700 rpm. As the reactor temperature approached 85° C., ethylene addition was begun, and the set point of 90° C. was rapidly attained. The reactor was held at 90° C. for 60 min. The yield was 27,776 kg polymer/mol Ti/hr. See Example 14 in Table 1.

A representative polymerization with MET-I and sulfated alumina was conducted as follows. Approximately 2 mg of MET-I in 2 mL of toluene were mixed with 300 mg of sulfated alumina in 2 mL of toluene in a glass tube under nitrogen. After about one min, this slurry was added to the reactor at below 40° C. The reactor was sealed and 2 L of isobutane were added and the contents were stirred at 700 rpm. As the reactor temperature approached 85° C., ethylene addition was begun, and the set point of 90° C. was rapidly attained. The reactor was held at 90° C. for 60 min. The yield was 8,315 kg polymer/mol Ti/hr. See Example 26 in Table 1.

A representative polymerization with MET-J and sulfated alumina was conducted as follows. Approximately 2 mg of MET-J in 2 mL of toluene were mixed with 300 mg of sulfated alumina in 2 mL of toluene in a glass tube under nitrogen. After about one min, this slurry was added to the reactor at below 40° C. The reactor was sealed and 2 L of isobutane were added and the contents were stirred at 700 rpm. As the reactor temperature approached 85° C., ethylene addition was begun, and the set point of 90° C. was rapidly attained. The reactor was held at 90° C. for 60 min. The yield was 22,994 kg polymer/mol Ti/hr. See Example 27 in Table 1.

A representative copolymerization with MET-J, sulfated alumina, and hydrogen was conducted as follows. Approximately 2 mg of MET-J in 2 mL of toluene were mixed with 300 mg of sulfated alumina in 2 mL of toluene in a glass tube under nitrogen. After about one min, this slurry was added to the reactor at below 40° C. The reactor was sealed and 2 L of isobutane were added and the contents were stirred at 700 rpm. As the reactor temperature approached 85° C., 25 g of 1-hexene were added in with ethylene and hydrogen (delta 45 psi or 0.31 MPa), and the set point of 90° C. was rapidly attained. The reactor was held at 90° C. for 60 min. The yield was 18,794 kg polymer/mol Ti/hour. See Example 52 in Table 1.

A representative polymerization with MET-K and sulfated alumina was conducted as follows. Approximately 2 mg of MET-K in 2 mL of toluene were mixed with 300 mg of sulfated alumina in 2 mL of toluene in a glass tube under nitrogen. After about one min, this slurry was added to the reactor at below 40° C. The reactor was sealed and 2 L of isobutane were added and the contents were stirred at 700 rpm. As the reactor temperature approached 85° C., ethylene addition was begun, and the set point of 90° C. was rapidly attained. The reactor was held at 90° C. for 60 min. The yield was 27,623 kg polymer/mol Ti/hr. See Example 28 in Table 1.

Using 1H-NMR analysis, the ratio of vinyl end groups to saturated end groups was determined for certain polymers produced, and abbreviated V/S in Table 1. For these polymers, the ratio of vinyl end groups to saturated end groups was in a range from 0.6 to 0.9.

Figure 5:
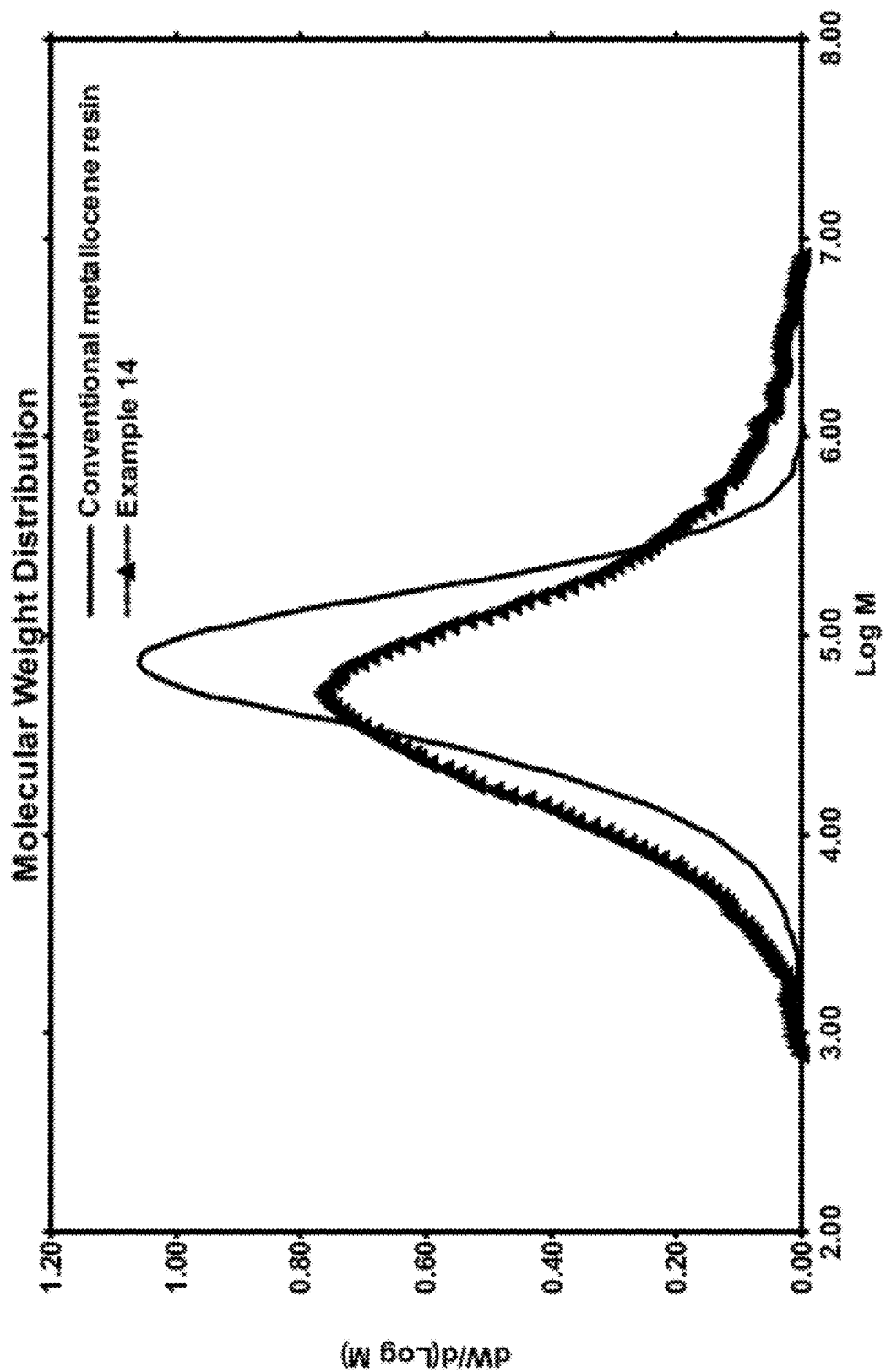
FIG. 5 presents a plot of the molecular weight distributions of the polymer of Example 14 and of a comparative polymer produced using a standard metallocene catalyst system.

FIG. 5 compares the molecular weight distribution of the polymer of Example 14, produced using hybrid metallocene MET-E, and that of a conventional polymer produced using a standard metallocene catalyst system. The molecular weight distribution is much broader for Example 14.

Figure 6:
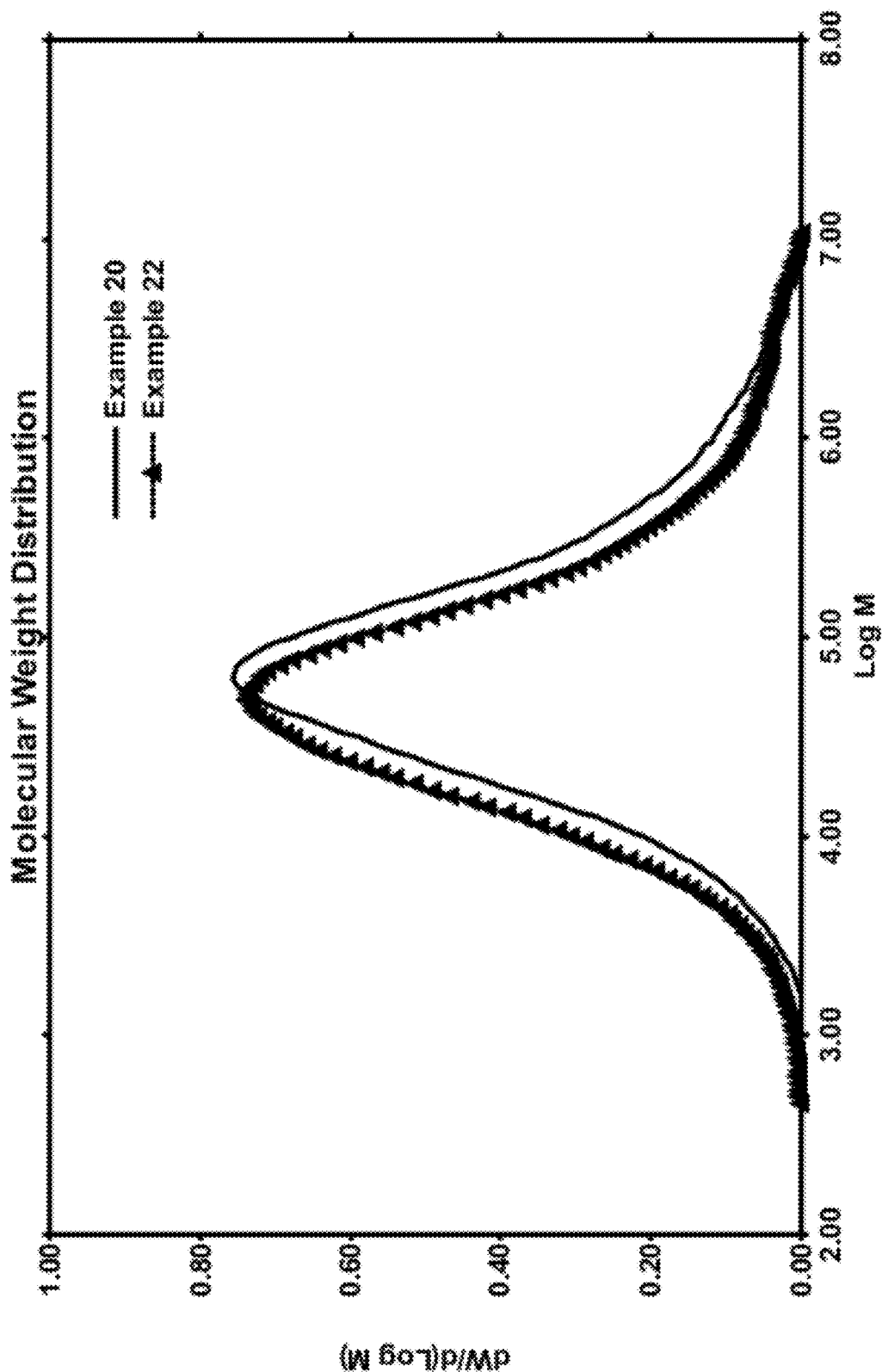
FIG. 6 presents a plot of the molecular weight distributions of the polymers of Examples 20 and 22.
Figure 7:
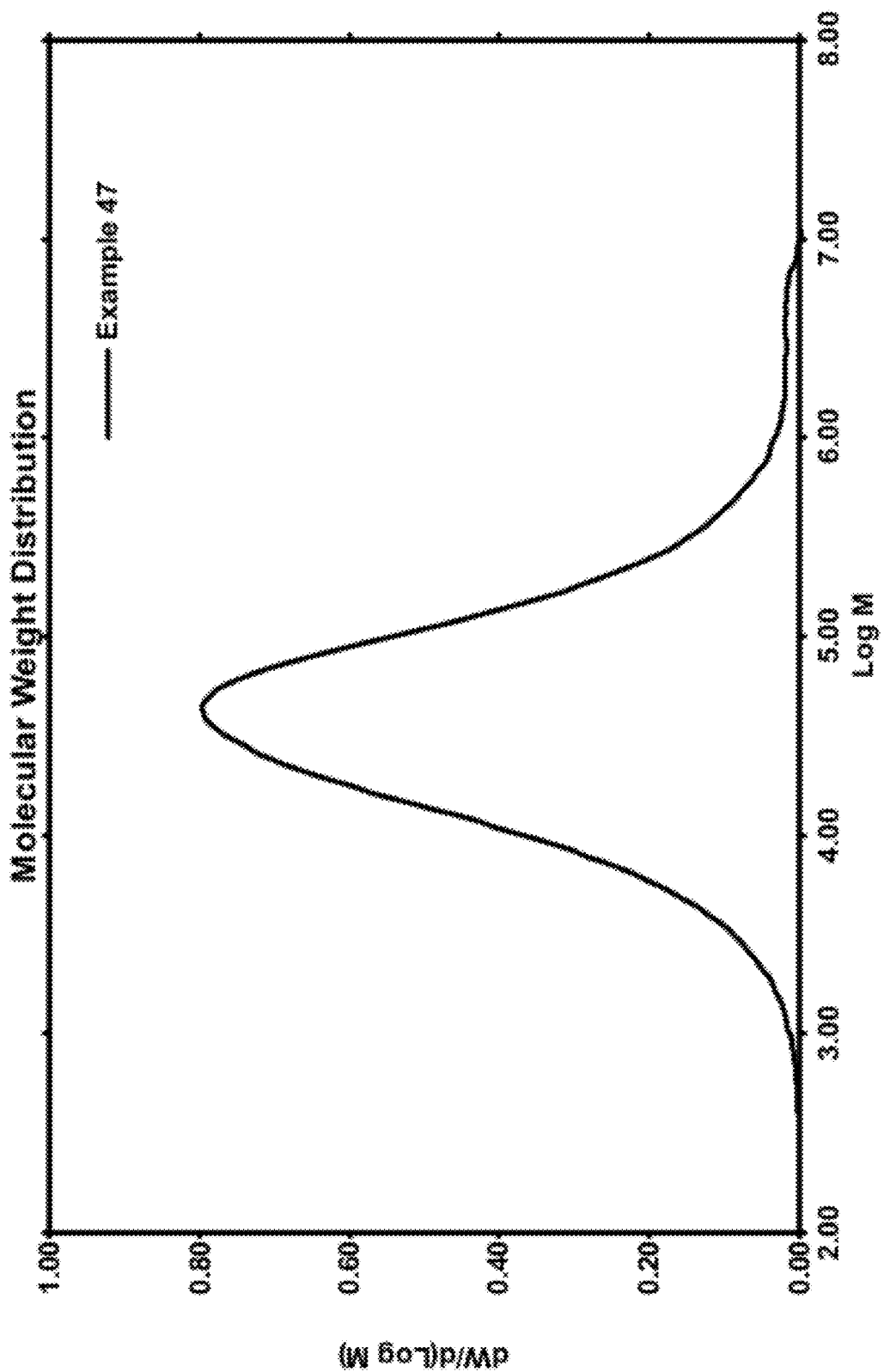
FIG. 7 presents a plot of the molecular weight distribution of the polymer of Example 47.

FIG. 6 compares the molecular weight distributions of the polymers of Examples 20 and 22, while FIG. 7 illustrates the molecular weight distribution of the polymer of Example 47. Each of these polymers had a relatively broad molecular weight distribution.

Figure 8:
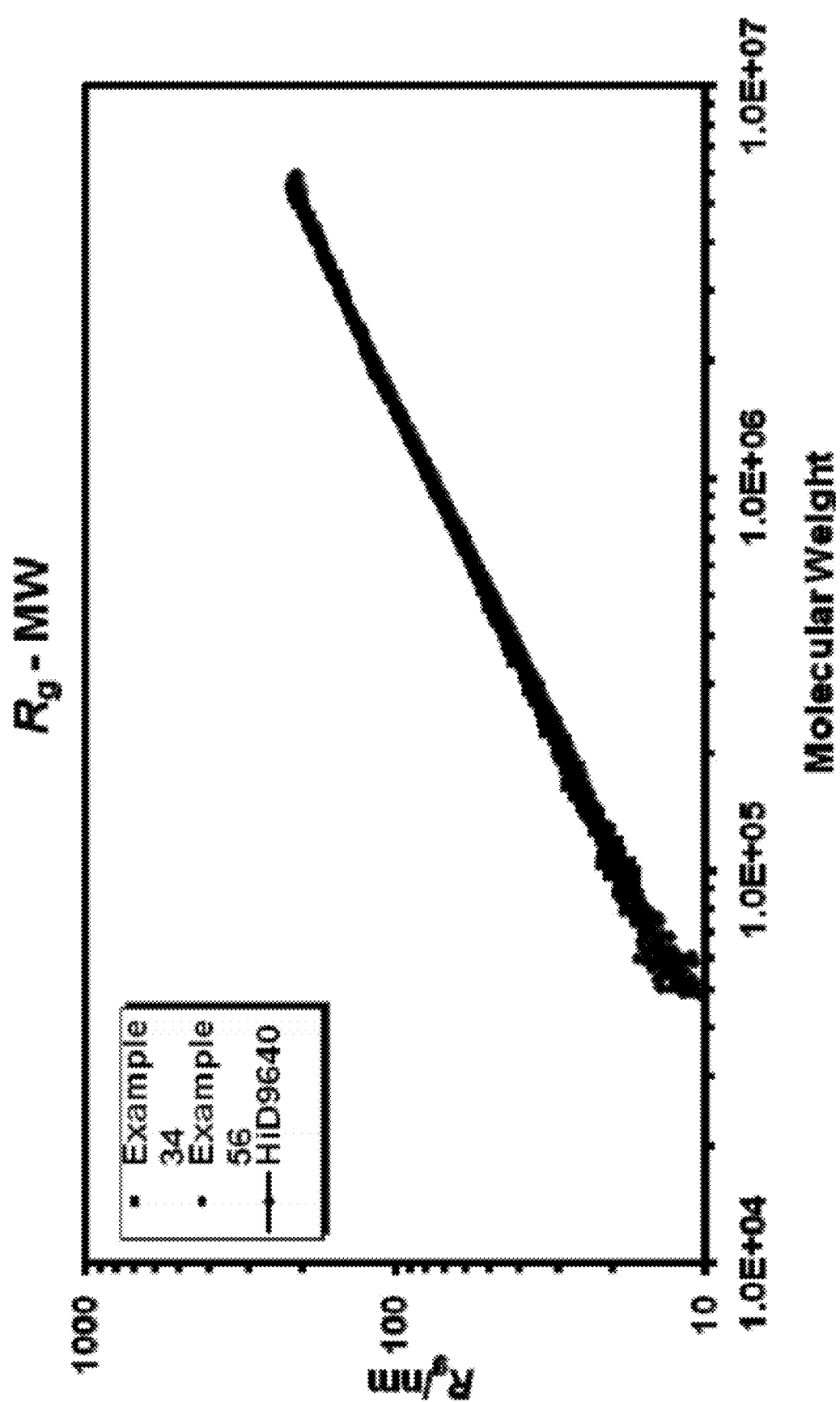
FIG. 8 presents a plot of the radius of gyration versus the logarithm of molecular weight for a linear standard and the polymers of Examples 34 and 56.

FIG. 8 illustrates the radius of gyration versus the logarithm of the molecular weight for a linear standard and the polymers of Examples 34 and 56, with data from SEC-MALS. FIG. 8 demonstrates these polymers were substantially linear polymers with minimal amounts of LCB's (long chain branches).

TABLE 1

Polymerization Conditions and Polymer Properties for Examples 7-61.

| Example | Catalyst Type | Catalyst Weight (mg) | TIBA (mL) | Sulfated Alumina (g) | 1-Hexene (g) | $H_2$ deltaP (MPa) | Ethylene (MPa) | Temp (° C.) | Time (min) |
|---|---|---|---|---|---|---|---|---|---|
| 7 | A | 2 | 0.5 | 0.3 | | | 2.8 | 90 | 60 |
| 8 | B | 2 | 0.5 | 0.3 | | | 2.8 | 90 | 60 |
| 9 | C | 2 | 0.5 | 0.3 | | | 2.8 | 90 | 60 |
| 10 | D | 2 | 0.5 | 0.3 | | | 2.8 | 90 | 60 |
| 11 | D | 2 | 0.5 | 0.01 | | 2.5 | 2.8 | 90 | 60 |
| 12 | E | 2 | 0.5 | 0.1 | | | 2.8 | 90 | 60 |
| 13 | E | 2 | 0.5 | 0.2 | | | 2.8 | 90 | 60 |
| 14 | E | 2 | 0.5 | 0.3 | | | 2.8 | 90 | 60 |
| 15 | E | 2 | 0.5 | 0.4 | | | 2.8 | 90 | 60 |
| 16 | E | 2 | 0.5 | 0.5 | | | 2.8 | 90 | 60 |
| 17 | E | 2 | 0 | 0.3 | | | 2.8 | 90 | 60 |
| 18 | E | 2 | 1 | 0.3 | | | 2.8 | 90 | 60 |
| 19 | E | 2 | 2 | 0.3 | | | 2.8 | 90 | 60 |
| 20 | E | 8 | 0.5 | 0.3 | | 0.8 | 2.9 | 80 | 60 |
| 21 | F | 2 | 0.5 | 0.3 | | | 2.8 | 90 | 60 |
| 22 | G | 2 | 0.5 | 0.3 | | | 2.8 | 90 | 60 |
| 23 | G | 2 | 0.5 | 0.3 | | 0.22 | 2.8 | 90 | 60 |
| 24 | H | 2 | 0.5 | 0.2 | | 0.12 | 2.8 | 90 | 60 |
| 25 | H | 2 | 0.5 | 0.2 | | 0.22 | 2.8 | 90 | 60 |
| 26 | I | 2 | 0.5 | 0.3 | | | 2.8 | 90 | 60 |
| 27 | J | 2 | 0.5 | 0.3 | | | 2.8 | 90 | 60 |
| 28 | K | 2 | 0.5 | 0.3 | | | 2.8 | 90 | 60 |
| 29 | K | 2 | 0.5 | 0.3 | | | 2.4 | 80 | 60 |
| 30 | K | 2 | 0.5 | 0.3 | | | 3.4 | 105 | 60 |
| 31 | K | 2 | 0.5 | 0.2 | | 0.12 | 2.8 | 90 | 60 |
| 32 | K | 2 | 0.5 | 0.2 | | 0.22 | 2.8 | 90 | 60 |

TABLE 1-continued

Polymerization Conditions and Polymer Properties for Examples 7-61.

| | | | | | | | | | | |
|---|---|---|---|---|---|---|---|---|---|---|
| 33 | C | 2 | 0.5 | 0.3 | 34 | | 2.0 | | 80 | 60 |
| 34 | D | 2 | 0.5 | 0.3 | 25 | | 2.8 | | 90 | 60 |
| 35 | D | 2 | 0.5 | 0.3 | 25 | 0.12 | 2.8 | | 90 | 60 |
| 36 | D | 2 | 0.5 | 0.3 | 25 | 0.22 | 2.8 | | 90 | 60 |
| 37 | D | 2 | 0.5 | 0.3 | 25 | 0.31 | 2.8 | | 90 | 60 |
| 38 | D | 2 | 0.5 | 0.3 | 25 | 0.41 | 2.8 | | 90 | 60 |
| 39 | D | 2 | 0.5 | 0.3 | 25 | 0.50 | 2.9 | | 90 | 60 |
| 40 | D | 2 | 0.5 | 0.3 | 57 | 0.46 | 2.8 | | 90 | 60 |
| 41 | D | 2 | 0.5 | 0.3 | 87 | 0.46 | 2.8 | | 90 | 60 |
| 42 | D | 2 | 0.5 | 0.3 | 118 | 0.46 | 2.8 | | 90 | 60 |
| 43 | D | 2 | 0.5 | 0.3 | 150 | 0.46 | 2.7 | | 90 | 60 |
| 44 | E | 8 | 0.5 | 0.3 | 25 | 0.80 | 2.9 | | 80 | 60 |
| 45 | G | 2 | 0.5 | 0.3 | 34 | | 2.0 | | 80 | 60 |
| 46 | G | 2 | 0.5 | 0.3 | 70 | | 2.0 | | 80 | 60 |
| 47 | G | 2 | 0.5 | 0.3 | 106 | | 2.0 | | 80 | 60 |
| 48 | H | 2 | 0.5 | 0.2 | 57 | | 2.8 | | 90 | 60 |
| 49 | H | 2 | 0.5 | 0.2 | 118 | | 2.8 | | 90 | 60 |
| 50 | J | 2 | 0.5 | 0.3 | 25 | | 2.8 | | 90 | 60 |
| 51 | J | 2 | 0.5 | 0.3 | 25 | 0.12 | 2.8 | | 90 | 60 |
| 52 | J | 2 | 0.5 | 0.3 | 25 | 0.31 | 2.8 | | 90 | 60 |
| 53 | J | 2 | 0.5 | 0.3 | 25 | 0.50 | 2.9 | | 90 | 60 |
| 54 | J | 2 | 0.5 | 0.3 | 25 | 0.92 | 2.9 | | 90 | 60 |
| 55 | J | 2 | 0.5 | 0.3 | 57 | 0.46 | 2.8 | | 90 | 60 |
| 56 | J | 2 | 0.5 | 0.3 | 87 | 0.46 | 2.8 | | 90 | 60 |
| 57 | J | 2 | 0.5 | 0.3 | 118 | 0.46 | 2.8 | | 90 | 60 |
| 58 | J | 2 | 0.5 | 0.3 | 150 | 0.46 | 2.7 | | 90 | 60 |
| 59 | K | 2 | 0.5 | 0.3 | 57 | | 2.4 | | 80 | 60 |
| 60 | K | 2 | 0.5 | 0.3 | 118 | | 2.4 | | 80 | 60 |
| 61 | K | 2 | 0.5 | 0.3 | 150 | | 2.4 | | 80 | 60 |

| Example | Catalyst Type | Catalyst Activity | MI (g/10 min) | HLMI (g/10 min) | Mn/1000 | Mw/1000 | Mz/1000 | Mw/Mn | Density (g/cc) | V/S |
|---|---|---|---|---|---|---|---|---|---|---|
| 7 | A | 10474 | 0.032 | 8.9 | | | | | | |
| 8 | B | 13359 | 0.003 | 8.2 | | | | | | |
| 9 | C | 24524 | | | | | | | | |
| 10 | D | 23363 | | 70.5 | 23.66 | 220.5 | 1690.1 | 9.32 | | |
| 11 | D | 23793 | 0.025 | 3.9 | 43.40 | 235.7 | 843.7 | 5.43 | | |
| 12 | E | 12597 | 0.05 | 18.0 | | | | | | |
| 13 | E | 16752 | 0.095 | 26.4 | | | | | | |
| 14 | E | 27776 | 0.16 | 115.9 | 21.75 | 157.7 | 1399.8 | 7.25 | | |
| 15 | E | 19350 | 0.149 | 72.4 | | | | | | |
| 16 | E | 20211 | 0.12 | 34.9 | | | | | | |
| 17 | E | N/A | | | | | | | | |
| 18 | E | 8541 | 0.336 | 75.1 | | | | | | |
| 19 | E | 14269 | 0.45 | 66.3 | | | | | | |
| 20 | E | 6269 | 0.025 | 13.6 | 32.74 | 245.8 | 2059.8 | 7.51 | 0.9631 | |
| 21 | F | 2777 | | | | | | | | |
| 22 | G | 21448 | 0.195 | 572.8 | 21.52 | 197.5 | 2059.2 | 9.18 | 0.9669 | |
| 23 | G | 12033 | 0.094 | 298.3 | | | | | | |
| 24 | H | 1729 | | | | | | | | |
| 25 | H | 1145 | | | | | | | | |
| 26 | I | 8315 | | 8.7 | | | | | | |
| 27 | J | 22994 | 0.02 | 15.3 | 25.59 | 216.0 | 1682.1 | 8.44 | | 0.85 |
| 28 | K | 27623 | 0.024 | 9.1 | 22.42 | 290.6 | 3162.9 | 12.96 | | |
| 29 | K | 11334 | too low | 1.6 | | | | | | |
| 30 | K | 18636 | 0.64 | 45.0 | 22.12 | 276.6 | 2610.8 | 12.5 | | |
| 31 | K | 9228 | | | | | | | | |
| 32 | K | 7121 | | | | | | | | |
| 33 | C | 6687 | | | | | | | | |
| 34 | D | 17960 | 0.47 | 39.6 | 24.62 | 171.9 | 1471.9 | 6.98 | 0.9536 | |
| 35 | D | 12219 | 0.038 | 38.4 | 22.33 | 205.2 | 2084.5 | 9.19 | 0.9516 | |
| 36 | D | 9425 | 0.474 | 120.1 | | | | | 0.9502 | |
| 37 | D | 10745 | 0.367 | 107.6 | | | | | | 0.67 |
| 38 | D | 9210 | 0.39 | 79.9 | | | | | | |
| 39 | D | 9885 | 0.35 | 168.7 | | | | | | |
| 40 | D | 8811 | 1.04 | 151.6 | 17.21 | 185.0 | 2239.3 | 10.75 | | |
| 41 | D | 11513 | 2.465 | 129.7 | 16.11 | 158.8 | 2333.6 | 9.86 | | |
| 42 | D | 9041 | 2.1 | 185.2 | | | | | | |
| 43 | D | 9763 | 1.57 | 138.9 | | | | | | |
| 44 | E | 7883 | 0.169 | 25.3 | 30.94 | 255.6 | 2438.4 | 8.26 | 0.9582 | |
| 45 | G | 9186 | | | 22.07 | 182.8 | 2301.9 | 8.28 | 0.9583 | |
| 46 | G | 14008 | 1.37 | 156.3 | 18.85 | 144.5 | 2008.7 | 7.67 | 0.9523 | |
| 47 | G | 10747 | 2.06 | 224.9 | 17.72 | 131.5 | 2027.8 | 7.42 | 0.9501 | |
| 48 | H | 1075 | | | | | | | | |
| 49 | H | 2360 | | | | | | | | |
| 50 | J | 21640 | 0.69 | 38.9 | 21.07 | 165.9 | 1531.9 | 7.88 | | |
| 51 | J | 16747 | 0.597 | 49.2 | | | | | | |

TABLE 1-continued

Polymerization Conditions and Polymer Properties for Examples 7-61.

| 52 | J | 18794 | 1.008 | 95.9  | 19.21 | 171.1 | 2051.8 | 8.91 |        |      |
|----|---|-------|-------|-------|-------|-------|--------|------|--------|------|
| 53 | J | 16347 | 1.46  | 126.2 |       |       |        |      |        |      |
| 54 | J | 9631  | 1.59  | 155.5 |       |       |        |      |        |      |
| 55 | J | 13276 | 1.47  | 123.3 |       |       |        |      |        |      |
| 56 | J | 9284  | 1.31  | 125.8 | 17.61 | 165.8 | 1929.9 | 9.41 | 0.9563 |      |
| 57 | J | 6994  | 0.92  | 104.6 |       |       |        |      | 0.9547 |      |
| 58 | J | 10100 | 5.29  | 250.9 |       |       |        |      | 0.9516 | 0.66 |
| 59 | K | 14965 | 0.09  | 10.1  |       |       |        |      |        |      |
| 60 | K | 17092 | 0.25  | 18.3  |       |       |        |      |        |      |
| 61 | K | 12899 | 0.24  | 31.8  |       |       |        |      |        |      |

$X^1$ and $X^2$ are Cl; and $X^3$ is a substituted or unsubstituted cyclopentadienyl group.
21. The compound of claim 20, wherein any substituents on $X^3$ independently are a hydrogen atom, a methyl group, an ethyl group, a propyl group, a n-butyl group, a t-butyl group, or a hexyl group.
22. The compound of claim 11, wherein the compound is:
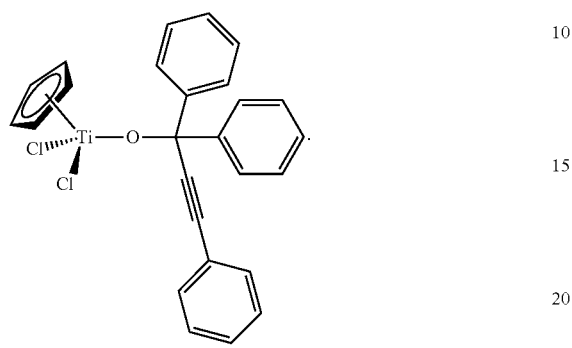

We claim:

1. A compound having the formula:

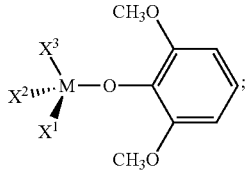

(III)

wherein:

M is Zr or Hf;

$X^1$ and $X^2$ independently are a halide or a substituted or unsubstituted aliphatic, aromatic, or cyclic group, or a combination thereof; and $X^3$ is a substituted or unsubstituted cyclopentadienyl, indenyl, or fluorenyl group, wherein any substituents on $X^3$ independently are a hydrogen atom or a substituted or unsubstituted aliphatic, aromatic, or cyclic group, or a combination thereof.

2. The compound of claim 1, wherein M is Hf.

3. The compound of claim 1, wherein M is Zr.

4. The compound of claim 1, wherein $X^1$ and $X^2$ independently are a methyl group, a phenyl group, a benzyl group, or a halide.

5. The compound of claim 1, wherein $X^1$ and $X^2$ independently are a halide.

6. The compound of claim 1, wherein $X^3$ is a substituted or unsubstituted cyclopentadienyl group.

7. The compound of claim 1, wherein $X^3$ is a substituted or unsubstituted indenyl group.

8. The compound of claim 1, wherein any substituents on $X^3$ independently are a hydrogen atom, a methyl group, an ethyl group, a propyl group, a n-butyl group, a t-butyl group, or a hexyl group.

9. The compound of claim 1, wherein:

M is Zr;

$X^1$ and $X^2$ are Cl; and $X^3$ is a substituted or unsubstituted cyclopentadienyl group.

10. The compound of claim 9, wherein any substituents on $X^3$ independently are a hydrogen atom, a methyl group, an ethyl group, a propyl group, a n-butyl group, a t-butyl group, or a hexyl group.

11. A compound having the formula:

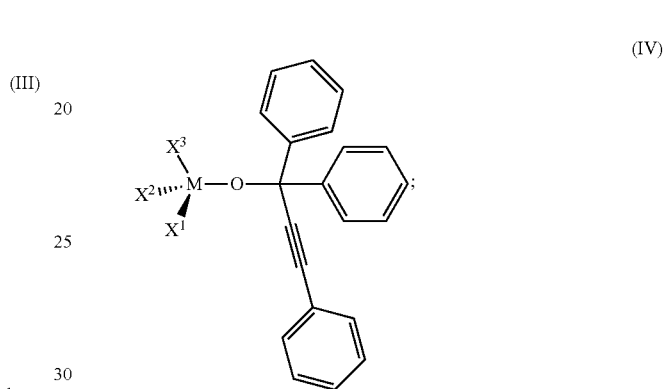

(IV)

wherein:

M is Zr, Hf, or Ti;

$X^1$ and $X^2$ independently are a halide or a substituted or unsubstituted aliphatic, aromatic, or cyclic group, or a combination thereof; and $X^3$ is a substituted or unsubstituted cyclopentadienyl, indenyl, or fluorenyl group, wherein any substituents on $X^3$ independently are a hydrogen atom or a substituted or unsubstituted aliphatic, aromatic, or cyclic group, or a combination thereof.

12. The compound of claim 11, wherein M is Ti.

13. The compound of claim 11, wherein M is Zr.

14. The compound of claim 11, wherein $X^1$ and $X^2$ independently are a methyl group, a phenyl group, a benzyl group, or a halide.

15. The compound of claim 11, wherein $X^1$ and $X^2$ independently are a halide.

16. The compound of claim 11, wherein $X^3$ is a substituted or unsubstituted cyclopentadienyl group.

17. The compound of claim 11, wherein $X^3$ is a substituted or unsubstituted indenyl group.

18. The compound of claim 11, wherein any substituents on $X^3$ independently are a hydrogen atom, a methyl group, an ethyl group, a propyl group, a n-butyl group, a t-butyl group, or a hexyl group.

19. The compound of claim 11, wherein:

M is Ti;

$X^1$ and $X^2$ independently are a methyl group, a phenyl group, a benzyl group, or a halide; and $X^3$ is a substituted or unsubstituted cyclopentadienyl group.

20. The compound of claim 11, wherein:

M is Ti;